United States Patent
Hayashi et al.

(10) Patent No.: US 11,839,654 B2
(45) Date of Patent: *Dec. 12, 2023

(54) COMBINATION THERAPY

(71) Applicant: Eli Lilly and Company, Indianapolis, IN (US)

(72) Inventors: Mansuo Lu Hayashi, Carmel, IN (US); Michael Carl Irizarry, Carmel, IN (US); Hugh Nuthall, Yateley (GB)

(73) Assignee: Eli Lilly and Company, Indianapolis, IN (US)

( * ) Notice: Subject to any disclaimer, the term of this patent is extended or adjusted under 35 U.S.C. 154(b) by 89 days.

This patent is subject to a terminal disclaimer.

(21) Appl. No.: 17/141,667

(22) Filed: Jan. 5, 2021

(65) Prior Publication Data

US 2021/0121565 A1    Apr. 29, 2021

Related U.S. Application Data

(63) Continuation of application No. PCT/US2019/043420, filed on Jul. 25, 2019.

(60) Provisional application No. 62/712,519, filed on Jul. 31, 2018.

(51) Int. Cl.
| | |
|---|---|
| A61K 39/395 | (2006.01) |
| A61P 25/28 | (2006.01) |
| A61K 31/454 | (2006.01) |
| A61K 39/00 | (2006.01) |

(52) U.S. Cl.
CPC ........ *A61K 39/3955* (2013.01); *A61K 31/454* (2013.01); *A61P 25/28* (2018.01); *A61K 2039/505* (2013.01)

(58) Field of Classification Search
CPC .............. A61K 39/3955; A61K 31/454; A61K 2039/505; A61K 2300/00; A61P 25/28; C07D 417/14; C07D 2200/09; C07D 2200/13

See application file for complete search history.

(56) References Cited

U.S. PATENT DOCUMENTS

| | | | |
|---|---|---|---|
| 4,921,887 A | 5/1990 | Matsuo et al. | |
| 5,811,310 A | 9/1998 | Ghanbari et al. | |
| 7,161,060 B1 | 1/2007 | Duff et al. | |
| 7,238,788 B2 | 7/2007 | Lee | |
| 7,442,516 B2 | 10/2008 | Ohno et al. | |
| 7,446,180 B2 | 11/2008 | Novak | |
| 8,012,936 B2 | 9/2011 | Sigurdsson et al. | |
| 8,609,097 B2 | 12/2013 | Bohrmann et al. | |
| 8,647,631 B2 | 2/2014 | Pfeifer et al. | |
| 8,697,076 B2 | 4/2014 | Binder et al. | |
| 8,703,137 B2 | 4/2014 | Chain | |
| 8,771,693 B2 | 7/2014 | Lu et al. | |
| 8,778,343 B2 | 7/2014 | Kayed | |
| 8,926,974 B2 | 1/2015 | Griswold-Prenner et al. | |
| 8,940,272 B2 | 1/2015 | Nitsch et al. | |
| 8,980,270 B2 | 3/2015 | Griswold-Prenner et al. | |
| 8,980,271 B2 | 3/2015 | Griswold-Prenner et al. | |
| 9,051,367 B2 | 6/2015 | Griswold-Prenner et al. | |
| 9,120,781 B2 | 9/2015 | Li et al. | |
| 9,139,643 B2 | 9/2015 | Sigurdsson et al. | |
| 9,290,567 B2 | 3/2016 | Bohrmann et al. | |
| 9,304,138 B2 | 4/2016 | Pfeifer et al. | |
| 9,527,909 B2 | 12/2016 | Lu et al. | |
| 10,011,653 B2 | 7/2018 | Lu et al. | |
| 10,081,625 B2 | 9/2018 | Dreyfus et al. | |
| 10,377,750 B2 | 8/2019 | Dreyfus et al. | |
| 2007/0218491 A1 | 9/2007 | Vasan et al. | |
| 2008/0220449 A1 | 9/2008 | Vasan et al. | |
| 2012/0244174 A1 | 9/2012 | Chain | |
| 2013/0095492 A1 | 4/2013 | DeBernardis et al. | |
| 2013/0295021 A1 | 11/2013 | Chen et al. | |
| 2014/0056901 A1 | 2/2014 | Agadjanyan et al. | |
| 2014/0099303 A1 | 4/2014 | Griswold-Prenner et al. | |
| 2014/0099304 A1 | 4/2014 | Griswold-Prenner et al. | |
| 2014/0161875 A1 | 6/2014 | Winderickx et al. | |
| 2014/0255412 A1 | 9/2014 | Pfeifer et al. | |
| 2014/0294731 A1 | 10/2014 | Pfeifer et al. | |
| 2014/0294839 A1 | 10/2014 | Kuret et al. | |
| 2014/0302046 A1 | 10/2014 | Sigurdsson | |
| 2015/0004169 A1 | 1/2015 | Kayed | |
| 2015/0175682 A1 | 6/2015 | Pfeifer et al. | |
| 2015/0239963 A1 | 8/2015 | Griswold-Prenner et al. | |
| 2015/0252102 A1 | 9/2015 | Nitsch et al. | |
| 2015/0259406 A1 | 9/2015 | Pfeifer et al. | |

(Continued)

FOREIGN PATENT DOCUMENTS

| | | |
|---|---|---|
| EP | 0279454 A2 | 8/1988 |
| WO | 2004016655 A1 | 2/2004 |

(Continued)

OTHER PUBLICATIONS

Hastings NB et al. Inhibition of O-GlcNAcase leads to elevation of O-GlcNAc tau and reduction of tauopathy and cerebrospinal fluid tau in rTg4510 mice. Molecular Neurodegeneration (2017) 12:39, 16 pages. (Year: 2017).*
Asuni A., et al., J. of Neuroscience (2007) 27(34): 9115-9129.
Ahmed, Z et al., (2014) Acta Neuropathol. 27(5): 667-683.
Braak, H. et al., Acta Neuropathol (1991) 82:239-259.
Billingsley M. et al., Journal of Biochem. (1997) 323: 577-591.
Boutajangout, A. et al., Journal of Neurochem. (2011) 118: 658-667.
Carmel, G., et al., J. Biol. Chem (1996) 271:32789-32795.
Castillo-Carranza, D., et al., J. of Neuroscience (2014) 34 (12):4260-4272.
Chai X., et al. (2011) J Biol Chem. 30:286(39):34457-67.
Clavaguera, et al. (2009) Nature Cell Biol. 11, 909-913.

(Continued)

*Primary Examiner* — Kimberly Ballard
(74) *Attorney, Agent, or Firm* — Robert D. Shereda

(57) ABSTRACT

The present invention provides a method of treating a tau-mediated cognitive or neurodegenerative disease, comprising administering to a patient in need of such treatment an effective amount of an anti-Tau antibody and an effective amount of an OGA inhibitor.

6 Claims, No Drawings

Specification includes a Sequence Listing.

(56) References Cited

U.S. PATENT DOCUMENTS

| | | |
|---|---|---|
| 2016/0031871 A1 | 2/2016 | Yu et al. |
| 2016/0251420 A1* | 9/2016 | Hayashi ................. C12N 15/00 424/139.1 |

FOREIGN PATENT DOCUMENTS

| | | |
|---|---|---|
| WO | 2005/014579 A1 | 2/2005 |
| WO | 2005080986 A1 | 9/2005 |
| WO | 2010142423 A1 | 1/2010 |
| WO | 2010115483 A2 | 10/2010 |
| WO | 2010144711 A2 | 12/2010 |
| WO | 2011026031 A1 | 3/2011 |
| WO | 2012045882 A2 | 4/2012 |
| WO | 2012049570 A1 | 4/2012 |
| WO | 2013007839 A1 | 1/2013 |
| WO | 2013041962 A1 | 3/2013 |
| WO | 2013050567 A1 | 4/2013 |
| WO | 2013059786 A1 | 4/2013 |
| WO | 2013096380 A2 | 6/2013 |
| WO | 2013151762 A1 | 10/2013 |
| WO | 2014008404 A1 | 1/2014 |
| WO | 2014016737 A1 | 1/2014 |
| WO | 2014028777 A2 | 2/2014 |
| WO | 2014031697 A2 | 2/2014 |
| WO | 2014059442 A2 | 4/2014 |
| WO | 2014096321 A1 | 6/2014 |
| WO | 2014100600 A2 | 6/2014 |
| WO | 2014/159234 A1 | 10/2014 |
| WO | 2012106363 A2 | 10/2014 |
| WO | 2014165271 A2 | 10/2014 |
| WO | 2014200921 A1 | 12/2014 |
| WO | 2016/030443 A1 | 3/2016 |
| WO | 2017/106254 A1 | 6/2017 |

OTHER PUBLICATIONS

Collin, L., et al., Brain (2014) 137: 2834-2846.
Clavaguera, F. et al., (2014) Acta Neuropathol. 127: 299-301.
Clavaguera, F. et al., PNAS (2013), vol. 110, No. 23, 9535-9540 F. et al., PNAS (2013), vol. 110, No. 23, 9535-9540.
Frost, B., et al., J. of Biological Chemistry (2009) 284, No. 19, 12845-12852.
Falcon, B et al., (2015) J Biol Chem. 290(2):1049.
Goedert, M. et al., Trends in Neurosciences (2010) 33: 317-325.
Goedert, M. et al., Neuron (1989) 3: 519-526.
Gotz, J. et al., Biochimica et Biophysica Acta (2010) 1802: 860-871.
Gu J., et al., J. of Biol. Chem. (2013) 288:33081-33095.
Golde, T. et al., Neuron (2013) 80:254-256.
Guo J., et al., J. of Biol. Chem. (2011) 286(17):15317-15331.
Gerson, J., et al. Frontiers in Neurology (2013) vol. 4, Art.93, 1-10.
Haroutunian, V., et al., Neurobiol. of Aging (2007) 28:1-7.
Hyman, B. et al., (2012) Alzheimers Dement. 2012;8(1):1-13.
Ittner, A., et al., J. of Neurochem. (2015), 10.1111/jnc.12821.
Jicha, G. et al., J. Neurosci. Res. (1999), 55: 713-723.
Jicha, G. et al., (1997) J. Neurosci. Res., 48(2), 128-132.
Jicha, G. et al., J. Neurochem (1997) 69(5): 2087-2095.
Koerber, J. et al., Nature Biotechnology (2013) 31(10) 916-923.
Kfoury, N. et al., J Biol Chem. (2012) 287, No. 23, 19440-19451.
Kontsekova, E. et al., Alzheimer's Research & Therapy (2014) 6:45.
Liu, L. et al., www.plosone.org, (2012) vol. 7, Issue 2, e31302.
Lewis J. et al., (2000) Nat Genet. 25:402-405.
Lichrenberg-Kraag, B. et al., Biochem. (1992) 89:5384-5388.
Nakamura, K. et al., Cell (2012), 149: 232-244.
Otvos, L., et al., J. Neuroscience Res. (1994) 39:669-673.
Polydoro, M. et al., J. or Neuroscience (2013) 33(33): 13300-13311.
Pooler, A. et al., J. of Comparative Neurology (2013), 521: 4236-4248.
Ramsden, M., et al., (2005) J. Neuroscience. 25: 10637-10647.
Santa-Maria, I. et al., J Biol Chem. (2012) 287, No. 24, 20522-20533.
Saper, C.B. et al., Neuroscience (1987) vol. 23, No. 2, 389-398.
Sanders, D. et al., Neuron (2014), 82:1271-1288.
Santacruz K., et al., (2005) Science. 309(5733):476-81.
Selkoe, D. et al., (1991) Neuron. 6(4):487-498.
Uboga, N.V., et al., Neurobiol. of Aging (2000) 21:1-10.
Weaver, C., et al., Neurobiol. of Aging (2000) 21:719-727.
Wu J. et al., J Biol Chem. (2013) 288, No. 3, 1856-1870.
Wolozin, B. et al., Science (1986) 232:648-650.
Yanamandra, K. et al., Annals of Clin. and Translational Neurology (2015) 2(3): 278-288.
Yanamandra,, K. et al., Neuron (2013) 80:402-414.
Zetterberg H. et al., (2013) Alzheimers Res Ther. 5(2):9.
Jonas Bostrum, et al., *J. Med. Chem.*, (2012); pp. 1817-1830; vol. 55.
Chen, et al., "Discovery of new acetylcholinesterase and butyrylcholinesterase inhibitors through structure based virtual screening," RSC Adv., 2017, 7, 3429-3438.
Somani, et al., "Oxadiazole: A biologically important heterocycle" Der Pharma Chemica; 2009, 1 (1): 130-140.
Rudikoff, et al, Proc Natl Acad Sci USA 1982; 79:1979-1983.
Pascalis et al., The Journal of Immunology, 2002; 169: 3076-3084.
MacCallum et al., J. Mol. Biol., 1996; 262: 732-745.
Casset et al., BBRC. 2003; 307: 198-205.
Vajdos et al., J. Mol. Med., 2002; 320: 415-428.
Holmes et al., Mol. Immunol., 2007; 44: 1075-1084.
Wu et al.,J. Mol. Biol.,1999; 294: 151-162.
Pawson et al., Science, 2003, 300:445-452.
Alaoui-Ismaili et al., Cytokine Growth Factor Rev. 2009; 20:501-507.
Förster, S., Welleford, A. S., Triplett, J. C., Sultana, R., Schmitz, B., & Butterfield, D. A. (2014). Increased O-GlcNAc levels correlate with decreased O-GlcNAcase levels in Alzheimer disease brain. *Biochimica et Biophysica Acta (BBA)-Molecular Basis of Disease*, 1842(9), 1333-1339.
Chemical Abstract Number [1797647-11-0]; Commercial Source-Aurora Fine Chemicals, 7929 Silverton Ave. Suite 609, San Diego, CA, 92126; Order No. A35.639.184; entered STN Jul. 9, 2015.
Smith, S. M., Struyk, A., Jonathan, D., Declercq, R., Marcus, J., Toolan, D., . . . & Schoepp, D. (2016). O2-13-04: Early Clinical Results and Preclinical Validation of the O-Glcnacase (OGA) Inhibitor Mk-8719 as a Novel Therapeutic for the Treatment of Tauopathies. *Alzheimer's & Dementia*, 12, P261-P261.
NIH Fact Sheet, Progressive Supranuclear Palsy, Feb. 27, 2018.
Alzheimer Association.org Feb. 27, 2018, Latest Treatment for Alzheimer.

* cited by examiner

COMBINATION THERAPY

The present invention relates to a combination of an anti-Tau antibody and an O-GlcNAcase ("OGA") inhibitor, and to methods of using the same for the treatment of physiological disorders characterized by tau-mediated neurodegeneration (also referred to herein as "tauopathies"), such as Alzheimer's disease (AD), Progressive Supranuclear Palsy ("PSP") and Corticobasal Syndrome ("CBS").

AD, PSP and CBS are devastating neurodegenerative diseases pathologically characterized by aberrant tau aggregation, with AD alone affecting millions of people worldwide. Neuroanatomical progression of tau aggregation in neurodegenerative diseases such as AD, PSP and CBS suggests that tau fibril aggregation propagates along neuronal networks, resulting in destabilization of microtubules and ultimately localized impaired neuronal function. In view of the currently approved agents on the market which afford only transient, symptomatic, benefits to the patient, there is a significant unmet need in the treatment of tauopathies such as AD, PSP and CBS.

Tau is an axonal microtubule binding protein that promotes microtubule assembly and stability. The density and neuroanatomical localization of tau aggregation correlates strongly with AD, PSP and CBS neurologic symptoms and disease progression. For example, the number of NFTs in the brains of individuals with AD has been found to correlate closely with the severity of the disease, suggesting tau has a key role in neuronal dysfunction and neurodegeneration (Nelson et al., *J Neuropathol Exp Neurol.*, 71(5), 362-381 (2012)). Tau pathology has also been shown to correlate with disease duration in PSP; cases with a more aggressive disease course have a higher tau burden than cases with a slower progression. (Williams et al., *Brain*, 130, 1566-76 (2007)).

Moreover, animal model studies have shown tau aggregates spread across neuronal synapse junctions and sequester monomeric (native or non-aggregated) tau, inducing tau aggregate formation. Neuroanatomical progression of tau aggregation and accumulation in neurodegenerative diseases, such as AD, suggests that tau fibril aggregation propagates along neuronal networks, ultimately resulting in destabilization of microtubules and localized impaired neuronal function. This suggests that even small reductions in tau aggregation and accumulation might result in a long-term significant reduction in intraneuronal neurofibrillary tangles (NFTs), thus providing therapeutic benefits, particularly in the treatment of AD.

Additionally, recent studies (Yuzwa et al., *Nat Chem Biol*, 4(8), 483-490 (2008)) support the therapeutic potential of OGA inhibitors to limit tau hyperphosphorylation and intraneuronal aggregation into pathological tau, such as NFTs, for the treatment of AD and related tauopathies. Specifically, the OGA inhibitor Thiamet-G has been linked in slowing motor neuron loss in the JNPL3 tau mouse model (Yuzwa et al., *Nat Chem Biol*, 8, 393-399 (2012)) and to a reduction in tau pathology and dystrophic neurites in the Tg4510 tau mouse model (Graham et al., *Neuropharmacology*, 79, 307-313 (2014)).

A combination of an antibody which specifically binds tau aggregates and which reduces the propagation of tau aggregate formation (referred to herein as "anti-Tau antibodies") with an OGA inhibitor is desired to provide treatment for tauopathies such as AD and PSP. Such combination will also preferably be more effective than either molecule alone. For example, treatment with such combination may allow for use of lower doses of either or both molecule as compared to each molecule used alone, potentially leading to lower side effects (or a shorter duration of one or the other therapy) while maintaining efficacy. It is believed that the novel combination provided herein will limit tau hyperphosphorylation and reduce tau aggregation into pathological tau and propagation thereof for the treatment of tauopathies.

Accordingly, the present invention provides a method of treating a cognitive or neurodegenerative disease, comprising administering to a patient in need of such treatment an effective amount of an anti-Tau antibody in combination with an effective amount of an OGA inhibitor. The present invention further provides a method of treating clinical or pre-clinical AD comprising administering to a patient in need of such treatment an effective amount of an anti-Tau antibody in combination with an effective amount of an OGA inhibitor. The present invention also provides a method of treating prodromal AD (sometimes also referred to as mild cognitive impairment, or MCI), mild AD, moderate AD and/or severe AD, comprising administering to a patient in need of such treatment an effective amount of an anti-Tau antibody in combination with an effective amount of an OGA inhibitor.

The present invention further provides a method of slowing cognitive decline in a patient diagnosed with pre-clinical AD or clinical AD, comprising administering to a patient in need of such treatment an effective amount of an anti-Tau antibody in combination with an effective amount of an OGA inhibitor. The present invention further provides a method of slowing functional decline in a patient diagnosed with pre-clinical AD or clinical AD, comprising administering to a patient in need of such treatment an effective amount of an anti-Tau antibody in combination with an effective amount of an OGA inhibitor. The present invention further provides a method of preventing memory loss or cognitive decline in asymptomatic patients with low levels of NFTs in the brain, comprising administering an effective amount of an anti-Tau antibody in combination with an effective amount of an OGA inhibitor.

In another embodiment the present invention provides a method of treating asymptomatic patients known to have an Alzheimer's disease-causing genetic mutation, comprising administering an effective amount of an anti-Tau antibody in combination with an effective amount of an OGA inhibitor. Another embodiment of the present invention provides a method for the prevention of the progression of mild cognitive impairment to AD, comprising administering to a patient in need of such treatment an effective amount of an anti-Tau antibody in combination with an effective amount of an OGA inhibitor.

The present embodiments also provide an anti-Tau antibody, for use in simultaneous, separate, or sequential combination with an OGA inhibitor, for use in therapy.

The invention further provides a pharmaceutical composition comprising an anti-Tau antibody, with one or more pharmaceutically acceptable carriers, diluents, or excipients, in combination with a pharmaceutical composition of an OGA inhibitor, with one or more pharmaceutically acceptable carriers, diluents, or excipients.

In addition, the invention provides a kit, comprising an anti-Tau antibody, and an OGA inhibitor. The invention further provides a kit, comprising a pharmaceutical composition, comprising an anti-Tau antibody, with one or more pharmaceutically acceptable carriers, diluents, or excipients, and a pharmaceutical composition, comprising an OGA inhibitor with one or more pharmaceutically acceptable carriers, diluents, or excipients. As used herein, a "kit" includes separate containers of each component, wherein one component is an anti-Tau antibody, and another component is an OGA inhibitor, in a single package. A "kit" may also include separate containers of each component, wherein one component is an anti-Tau antibody, and another component is an OGA inhibitor, in separate packages with instructions to administer each component as a combination.

The invention further provides the use of an anti-Tau antibody, for the manufacture of a medicament for the treatment of AD, mild AD, prodromal AD or for the prevention of the progression of mild cognitive impairment to AD wherein the medicament is to be administered simultaneously, separately or sequentially with an OGA inhibitor.

In an embodiment of the present invention, the anti-Tau antibody comprises a heavy chain (HC) and a light chain (LC), wherein the HC comprises a heavy chain variable region (HCVR) and the LC comprises a light chain variable region (LCVR), said HCVR comprising complementarity determining regions (CDRs) HCDR1, HCDR2 and HCDR3 and said LCVR comprising CDRs LCDR1, LCDR2 and LCDR3. According to particular embodiments of the anti-Tau antibodies of the present invention, the amino acid sequence of LCDR1 is given by SEQ ID NO.3, the amino acid sequence of LCDR2 is given by SEQ ID NO.4, the amino acid sequence of LCDR3 is given by SEQ ID NO.5, the amino acid sequence of HCDR1 is given by SEQ ID NO.6, the amino acid sequence of HCDR2 is given by SEQ ID NO.7, and the amino acid sequence of HCDR3 is given by SEQ ID NO.8. In an embodiment, the present invention provides a monoclonal antibody that binds human tau, comprising a LCVR and a HCVR, wherein the amino acid sequence of the LCVR is given by SEQ ID NO.9 and the amino acid sequence of the HCVR is given by SEQ ID NO.10. In a further embodiment, the present invention provides a monoclonal antibody that binds human tau, comprising a light chain (LC) and a heavy chain (HC), wherein the amino acid sequence of the LC is given by SEQ ID NO.1 and the amino acid sequence of the HC is given by SEQ ID NO.2.

The anti-Tau antibodies of the present invention may be prepared and purified using known methods. For example, cDNA sequences encoding a HC (for example the amino acid sequence given by SEQ ID NO.2), such as the cDNA sequence given by SEQ ID NO.11, and a LC (for example, the amino acid sequence given by SEQ ID NO.1), such as the cDNA sequence given by SEQ ID NO.12, may be cloned and engineered into a GS (glutamine synthetase) expression vector. The engineered immunoglobulin expression vector may then be stably transfected into CHO cells. As one of skill in the art will appreciate, mammalian expression of antibodies will result in glycosylation, typically at highly conserved N-glycosylation sites in the Fc region. Stable clones may be verified for expression of an antibody specifically binding to tau aggregates. Positive clones may be expanded into serum-free culture medium for antibody production in bioreactors. Media, into which an antibody has been secreted, may be purified by conventional techniques. For example, the medium may be conveniently applied to a Protein A or G Sepharose FF column that has been equilibrated with a compatible buffer, such as phosphate buffered saline. The column is washed to remove nonspecific binding components. The bound antibody is eluted, for example, by pH gradient and antibody fractions are detected, such as by SDS-PAGE, and then pooled. The antibody may be concentrated and/or sterile filtered using common techniques. Soluble aggregate and multimers may be effectively removed by common techniques, including size exclusion, hydrophobic interaction, ion exchange, or hydroxyapatite chromatography. The product may be immediately frozen, for example at −70° C., or may be lyophilized.

The anti-Tau antibodies of the present invention bind human tau. In an embodiment, the anti-Tau antibodies of the present invention bind a conformational epitope of human tau. In a particular embodiment, the conformational epitope of human tau includes amino acid residues 7-9 and 312-322 of human tau, wherein the amino acid sequence of the human tau is given by SEQ ID NO.13.

As used herein, an "antibody" is an immunoglobulin molecule comprising two Heavy Chain (HC) and two Light Chain (LC) interconnected by disulfide bonds. The amino terminal portion of each LC and HC includes a variable region responsible for antigen recognition via the complementarity determining regions (CDRs) contained therein. The CDRs are interspersed with regions that are more conserved, termed framework regions. Assignment of amino acids to CDR domains within the LCVR and HCVR regions of the antibodies of the present invention is based on the well-known numbering conventions such as the following: Kabat, et al., Ann. NY Acad. Sci. 190:382-93 (1971); Kabat et al., Sequences of Proteins of Immunological Interest, Fifth Edition, U.S. Department of Health and Human Services, NIH Publication No. 91-3242 (1991); and North numbering convention (North et al., A New Clustering of Antibody CDR Loop Conformations, Journal of Molecular Biology, 406:228-256 (2011)).

In particular embodiments of the present invention, the antibodies and antibody fragments, or the nucleic acids encoding same, may be provided in isolated form. As used herein, the term "isolated" refers to a protein, peptide, or nucleic acid that is not found in nature and which is free or substantially free from other macromolecular species found in a cellular environment. "Substantially free", as used herein, means the protein, peptide or nucleic acid of interest comprises more than 80% (on a molar basis) of the macromolecular species present, preferably more than 90% and more preferably more than 95%.

Following expression and secretion of the antibodies and antibody fragments of the present invention, the medium is clarified to remove cells and the clarified media is purified using any of many commonly-used techniques. Purified antibodies and antibody fragments may be formulated into pharmaceutical compositions according to well-known methods for formulating proteins and antibodies for parenteral administration, particularly for subcutaneous, intrathecal, or intravenous administration. The antibodies and antibody fragments may be lyophilized, together with appropriate pharmaceutically-acceptable excipients, and then later reconstituted with a water-based diluent prior to use. Alternatively, the antibodies and antibody fragments may be formulated in an aqueous solution and stored prior to use. In either case, the stored form and the injected form of the pharmaceutical compositions of the antibodies and antibody fragments will contain a pharmaceutically-acceptable excipient or excipients, which are ingredients other than the antibodies and antibody fragments. Whether an ingredient is pharmaceutically-acceptable depends on its effect on the safety and effectiveness or on the safety, purity, and potency of the pharmaceutical composition. If an ingredient is judged to have a sufficiently unfavorable effect on safety or effectiveness (or on safety, purity, or potency) to warrant it not being used in a composition for administration to humans, then it is not pharmaceutically-acceptable to be used in a pharmaceutical composition of the antibody and antibody fragments.

The novel combinations and methods of the present invention include OGA inhibitors that are brain penetrant. In some embodiments of the novel combinations and methods of the present invention, the OGA inhibitor comprises a compound of Formula I:

Formula I

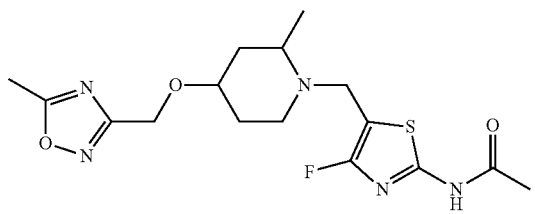

or a pharmaceutically acceptable salt thereof.

In some embodiments, the OGA inhibitor of the novel combinations and methods of the present invention is a compound of Formula Ia:

Formula Ia

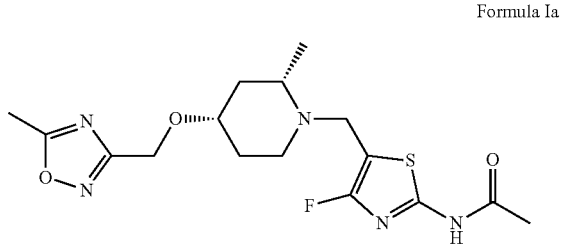 [SMILES: CC(=O)Nc1nc(F)c(CN2CC[C@H](OCc3noc(C)n3)C[C@@H]2C)s1]

or a pharmaceutically acceptable salt thereof.

Certain configurations of Formula I, which comprise embodiments of the OGA inhibitor of the novel combinations and methods of the present invention, further include:

Formula Ib

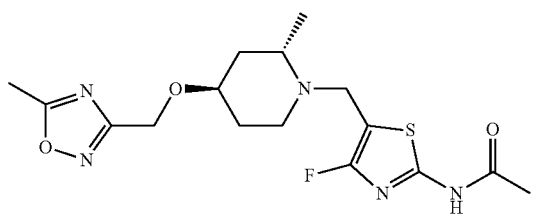

Formula Ic

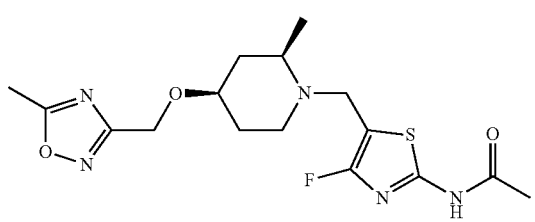

Formula Id

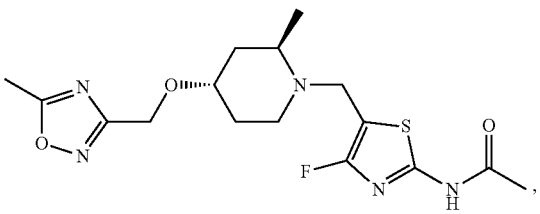

and pharmaceutically acceptable salts thereof.

The 5-methyl-1,2,4-oxadiazol-3-yl compound of Formula I wherein the methyl and oxygen substituents on the piperidine ring are in the cis or trans configuration, or pharmaceutically acceptable salt thereof, are included within the scope of the OGA inhibitor of the present novel combination. The present novel combination also contemplates all individual enantiomers and diastereomers, as well as mixtures of the enantiomers of 5-methyl-1,2,4-oxadiazol-3-yl compounds of the present invention, including racemates. Absolute configurations of 5-methyl-1,2,4-oxadiazol-3-yl compounds of the novel combinations and methods provided herein include:

N-[4-fluoro-5-[[(2S,4S)-2-methyl-4-[(5-methyl-1,2,4-oxadiazol-3-yl)methoxy]-1-piperidyl]methyl]thiazol-2-yl]acetamide, and pharmaceutically acceptable salts thereof; and N-[4-fluoro-5-[[(2S,4S)-2-methyl-4-[(5-methyl-1,2,4-oxadiazol-3-yl)methoxy]-1-piperidyl]methyl]thiazol-2-yl]acetamide are particularly preferred.

5-methyl-1,2,4-oxadiazol-3-yl OGA inhibitor compounds of the present invention, or salts thereof, may be prepared by a variety of procedures known to one of ordinary skill in the art. One of ordinary skill in the art recognizes that the specific synthetic steps for each of the routes described may be combined in different ways, or in conjunction with steps from different schemes, to prepare compounds of the invention, or salts thereof. The products of each step below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art. Without limiting the scope of the invention, the following preparations, and examples are provided to further illustrate the invention. In addition, one of ordinary skill in the art appreciates that the compounds of Formulas Ia, Ib, Ic, and Id may be prepared by using starting material with the corresponding stereochemical configuration which can be prepared by one of skill in the art. For example, the preparations below utilize starting materials with the configuration corresponding ultimately to Formula Ia.

Preparation 1

Synthesis of tert-butyl N-(4-fluoro-5-formyl-thiazol-2-yl)carbamate

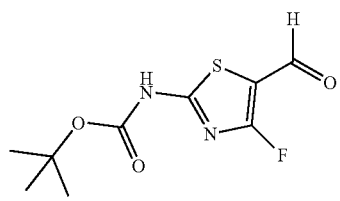 [SMILES: CC(C)(C)OC(=O)Nc1nc(F)c(C=O)s1]

Cesium fluoride (227 g, 1480 mmol) is added to a solution of tert-butyl N-(4-chloro-5-formyl-thiazol-2-yl)carbamate (38.8 g, 148 mmol; for preparation of tert-butyl N-(4-chloro-5-formyl-thiazol-2-yl)carbamate see for example, N. Masuda, et al., *Bioorg Med Chem*, 12, 6171-6182 (2004)) in DMSO (776 mL) at room temperature. The reaction mixture is stirred in a 145° C. heating block with an internal temperature of 133° C. for 48 hours, then the mixture is cooled in an ice-water bath. To the mixture is added saturated aqueous sodium bicarbonate solution (500 mL), brine (500 mL) and ethyl acetate (500 mL). The mixture is stirred at room temperature for 10 minutes, then is filtered through diatomaceous earth, washing with ethyl acetate (500 mL). The filtrate is transferred to a separating funnel and the layers are separated, then the aqueous layer is extracted with ethyl acetate (1 L). The combined organics are washed with brine (1 L), then the brine layer is extracted with ethyl acetate (300 mL). The combined organics are dried over sodium sulfate, filtered and concentrated to give a residue. The residue is passed through a pad of silica gel (330 g) eluting with 5% ethyl acetate in dichloromethane (1.5 L) and the filtrate is concentrated to give a residue (24.2 g).

The residue (32.7 g of combined lots, 133 mmol) is dissolved in isopropanol (303 mL), filtered and then is purified by SFC (Supercritical Fluid Chromatography) using an IC column (cellulose polysaccharide derivative: tris (3,5-dichlorophenylcarbamate, 30×250 mm, 5 u) with 10% IPA (no additive) at 180 mL/minute with 3 mL injections. The product-containing fractions are concentrated to give the title compound (16.1 g. MS m/z 247.0 (M+H).

Preparation 2

Synthesis N-(4-fluoro-5-formyl-thiazol-2-yl)acetamide (Method A)

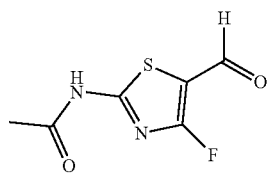

In a jacketed vessel, zinc bromide (91.9 g, 408 mmol) is added in one portion to a mixture of tert-butyl N-(4-fluoro-5-formyl-thiazol-2-yl)carbamate (33.5 g, 136 mmol) and dichloromethane (503 mL) at room temperature. The reaction mixture is stirred overnight at an internal temperature of 37° C., then the jacket temperature is set to −10° C. and tetrahydrofuran (111 mL) is added dropwise over 15 minutes, maintaining an internal temperature below 6° C. The jacket temperature is then set to −30° C. and pyridine (110 mL, 1360 mmol) is added dropwise over 5 minutes, maintaining an internal temperature below 5° C. The jacket temperature is set to 0° C. and acetic anhydride (116 mL, 1220 mmol) is added dropwise over 5 minutes. The reaction mixture is stirred overnight at an internal temperature of 37° C., then is cooled to room temperature and passed through a short pad of diatomaceous earth, eluting with tetrahydrofuran (500 mL). The filtrate is transferred to a flask and the mixture is concentrated to give a residue, which is concentrated from toluene (50 mL). To the residue is added a solution of citric acid monohydrate (57.2 g, 272 mmol) in water (400 mL) and 2-methyltetrahydrofuran (400 mL) and the mixture is stirred at 40° C. for 5 minutes, then is passed through a short pad of diatomaceous earth, eluting with 2-methyltetrahydrofuran (100 mL). The filtrate is transferred to a separating funnel and the layers are separated. The aqueous layer is extracted with 2-methyltetrahydrofuran (2×250 mL) and the combined organics are diluted with water (500 mL). To the mixture is added solid sodium bicarbonate portionwise over 5 minutes with stirring until gas evolution ceases. The mixture is transferred to a separating funnel and the layers are separated, then the aqueous layer is extracted with 2-methyltetrahydrofuran (200 mL and 100 mL). The combined organics are dried over sodium sulfate, filtered and concentrated to give a residue, which is diluted with 2-methyltetrahydrofuran (100 mL) and the mixture is passed through a short pad of silica gel (250 g), eluting with 2-methyltetrahydrofuran (2.5 L). The filtrate is concentrated to give a residue which is suspended in a 1:1 mixture of dichloromethane and heptane (202 mL). The mixture is stirred at room temperature for 30 minutes and then filtered. The filtered solid is dried under vacuum at 40° C. for 2 hours to give the title compound (18.0 g, 70%). MS m/z 189.0 (M+H).

Alternative Synthesis of N-(4-fluoro-5-formyl-thiazol-2-yl)acetamide (Method B)

Add dichloromethane (1325 g, 15.6 mol) to 2-amino-4-chlorothiazole-5-carbaldehyde (100 g, 0.61 mol) and pyridine (194.6 g, 2.46 mol), and cool to 0-5° C. Add acetic anhydride (188.4 g, 1.85 mol) dropwise, maintaining the temperature at 0-5° C. After addition is complete, adjust the temperature to 20-25° C. and stir for 41 hours. Concentrate under reduced pressure followed by addition of 35% aqueous HCl (200 mL) and water (1.5 L), maintaining the temperature at less than 40° C. Cool to 20-25° C. and stir for 18 hours. Filter the mixture and wash the collected solid with water. Dry the solids at 60-65° C. for 24 h to provide N-(4-chloro-5-formylthiazol-2-yl)acetamide (75 g, 0.4 mol).

Under an inert atmosphere, add sulfolane (1000 ml) to the N-(4-chloro-5-formylthiazol-2-yl)acetamide (50 g, 0.244 mol, prepared directly above), tetramethylammonium chloride (107.1 g, 0.977 mol), and cesium fluoride (370.6 g, 2.44 mmol). Heat to 130° C. and stir for 23 h. HPLC analysis shows 75% conversion with an in situ yield of 45% of the title compound.

Alternative Synthesis of N-(4-fluoro-5-formyl-thiazol-2-yl)acetamide (Method C)

Add 2-propanol (150 mL) to tetramethylammonium fluoride.tetrahydrate (10.2 g, 109.0 mmol) and concentrate the mixture to 2-3 volumes under vacuum with internal temperature maintained at 70° C. to remove water. Add 2-propanol (200 mL) and concentrate the mixture to 2-3 volumes under vacuum. Repeat two more times. Add DMF (200 mL) and concentrate to 2-3 volumes under vacuum. Add THF (200 mL) and concentrate to 2-3 volumes. Repeat two more times. Charge N-(4-chloro-5-formylthiazol-2-yl)acetamide (1.22 g, 5.96 mmol, prepared above in Method B) and DMF (12 ml). Heat to 110° C. and stir for 12 h. Cool reaction mixture to 25° C. Add 2-methyltetrahydrofuran (40 mL) and water (40 mL). The layers are separated and the aqueous layer was extracted with 2-methyltetrahydrofuran (40 mL). The layers were separated and the combined organic layers were washed with water (20 mL). The layers were separated and the organic layer was concentrated. Add ethyl acetate (20 mL) and water (5 mL). The layers were separated and the organic layer concentrated to remove solvent. Add ethyl acetate (2 mL) and heptane (2 mL) and filter. The filtered solid is dried under vacuum at 55° C. for 18 hours to give the title compound as a 93% mixture with N-(4-chloro-5-formylthiazol-2-yl)acetamide.

Preparation 3

Synthesis of tert-butyl (2S,4S)-4-hydroxy-2-methyl-piperidine-1-carboxylate

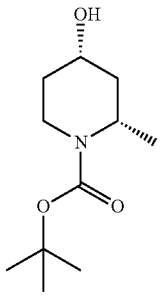

To a flask is added tert-butyl (2S)-2-methyl-4-oxo-piperidine-1-carboxylate (50 g, 234.44 mmol) and tetrahydrofuran (500 mL). The mixture is cooled to −65° C. under an atmosphere of nitrogen and lithium tri(sec-butyl)borohydride (304.77 mL, 304.77 mmol; 1 M in tetrahydrofuran) is added dropwise over 45 minutes, maintaining an internal temperature below −60° C. The reaction mixture is stirred at room temperature for 1 hour, then is cooled to −30° C. To the reaction mixture is added a mixture of water (25.34 mL) and tetrahydrofuran (100.16 mL), maintaining an internal temperature below −20° C. An aqueous solution of hydrogen peroxide (118.88 mL, 1.17 mol, 30 wt/wt %) in water (126.70 mL) is added dropwise over 1 hour, maintaining an internal temperature below 10° C. To the mixture is added aqueous hydrogen chloride solution (46.89 mL, 234.44 mmol, 5 M) and methyl t-butyl ether (1.00 L) and the mixture is warmed to room temperature. The layers are separated and the organic phase is stirred with a solution of sodium metabisulfite (222.84 g, 1.17 mol) in water (500 mL) for 10 minutes at room temperature. The layers are separated and the organic phase is dried over magnesium sulfate and concentrated. The residue is purified by flash chromatography (0-50% methyl t-butyl ether/isohexane, silica gel) and the product-containing fractions are combined and concentrated to give the title compound (40.4 g, 78%). ES/MS (m/e) 238 (M+Na).

Alternative Synthesis of tert-butyl (2S,4S)-4-hydroxy-2-methyl-piperidine-1-carboxylate

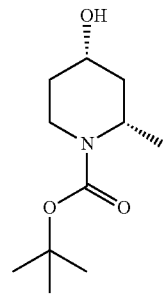

To a glass-lined reactor containing deionized water (460 L), and potassium dihydrogen phosphate (6.5 kg, 0.41 equiv) at 20° C. is charged DMSO (27.4 kg, 1.0 vol) and D-(+)-glucose monohydrate (28.9 kg, 1.25 equiv). The internal temperature is adjusted to 30° C., and the pH of the reaction is adjusted to 6.9 by addition of aqueous sodium hydroxide (8%, 15 L, 0.28 equiv). The reactor is charged with tert-butyl (2S)-2-methyl-4-oxo-piperidine-1-carboxylate (24.9 kg, 1.0 equiv (99.1% ee)), and the mixture is agitated at 30° C. for 15 min. Ketoreductase (KRED-130, 250 g, 1% w/w), glucose dehydrogenase (GDH-101, 250 g, 1% w/w), and NADP sodium salt (63 g, 0.25% w/w) are charged directly to the reaction mixture via an open port. The mixture is maintained at a temperature of 30° C. and pH 7.0±0.2 via addition of 8% aqueous NaHCO$_3$. After stirring for 16.5 h (99.5% conversion), the reaction is charged with Celite™ (12.5 kg, 50 w/w %) and toluene (125 L, 5 vol). After stirring for 30 min at 30° C., the mixture is transferred to another 2000 L reactor via an in-line GAF-filter (4 sock) over the period of 1 h. The mixture is allowed to stand 30 min without agitation, the layers are separated, and the aqueous layer is back-extracted with toluene (2×125 L). The combined organic layers are filtered (in-line GAF-filter), and the toluene mixture is washed with aqueous sodium chloride solution (25%, 125 L, 5 vol) at 25° C. The resulting toluene solution is azeotropically dried (partial vacuum, internal temp<60° C.) to 0.10 w/w % water, and cooled to 20° C. The mixture is filtered out of the reactor via a cartridge filter into clean drums under positive nitrogen pressure. The reaction mixture is then transferred from the drums into a 500 L glass lined vessel and concentrated under vacuum (<60° C.) to a target residual volume of 56 L (2.25 vol). n-Heptane (169 kg, 10 vol) is charged at 40° C., and the mixture is seeded with 25 g of tert-butyl (2S,4S)-4-hydroxy-2-methyl-piperidine-1-carboxylate. The resulting thick slurry is diluted with additional n-heptane (25 L, 1 vol) and cooled to 16° C. over 4 h. The product is isolated via centrifugation, washing with n-heptane (25 L per spin; 4 spins necessary), yielding 20.3 kg (81%; >99.9% ee) after drying for 11 h in a tray dryer at 30° C. ES/MS (m/e) 238 (M+Na).

Preparation 4

Synthesis of tert-butyl (2S,4S)-2-methyl-4-[(5-methyl-1,2,4-oxadiazol-3-yl)methoxy]piperidine-1-carboxylate

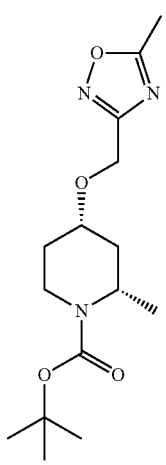 [SMILES: Cc1nc(CO[C@H]2CCN(C(=O)OC(C)(C)C)[C@@H](C)C2)no1]

3-(Chloromethyl)-5-methyl-1,2,4-oxadiazole (43.5 g, 301 mmol) is added to a solution of tert-butyl (2S,4S)-4-hydroxy-2-methyl-piperidine-1-carboxylate (29.5 g, 137 mmol) in acetonitrile (590 mL) at room temperature. The reaction mixture is stirred in an ice-water bath and sodium tert-butoxide (54.3 g, 548 mmol) is added in portions over 10 minutes, maintaining an internal temperature below 10° C. The reaction mixture is stirred in an ice-water bath at an internal temperature of 5° C. for 9 hours, then is warmed slowly to room temperature and is stirred overnight. The reaction mixture is cooled in an ice-water bath and saturated aqueous ammonium chloride solution (200 mL) is added over 5 minutes, maintaining an internal temperature below 10° C. during the addition. The mixture is then diluted with water (100 mL) and warmed to room temperature. The mixture is extracted with methyl tert-butyl ether (2×300 mL) and the combined organics are washed with brine (300 mL). The combined organics are dried over sodium sulfate, filtered and concentrated to give a residue. The residue is passed quickly through a pad of silica gel (300 g) eluting with methyl tert-butyl ether (1 L) and the filtrate is concentrated to give the title compound (46.5 g, 109%). MS m/z 334.0 (M+Na).

Alternative Synthesis of tert-butyl (2S,4S)-2-methyl-4-[(5-methyl-1,2,4-oxadiazol-3-yl)methoxy]piperidine-1-carboxylate

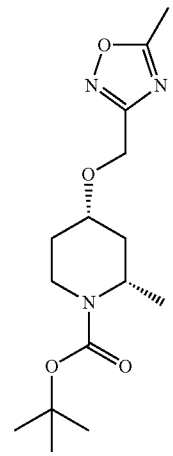 [SMILES: Cc1nc(CO[C@H]2CCN(C(=O)OC(C)(C)C)[C@@H](C)C2)no1]

To a solution of tert-butyl (2S,4S)-4-hydroxy-2-methyl-piperidine-1-carboxylate (0.25 g, 1.16 mmol) and 3-(chloromethyl)-5-methyl-1,2,4-oxadiazole (0.308 g, 2.32 mmol) in N,N-dimethylformamide (3 mL) under nitrogen at 0° C. is added portionwise sodium tert-butoxide (0.35 g, 3.5 mmol) over 5 min. The reaction mixture is stirred at rt for 10 min then at 40° C. for 12 h. The reaction mixture is cooled to room temperature then quenched with water (10 mL). The layers are separated and the aqueous phase is extracted with methyl tert-butyl ether (2×10 mL). The combined organic extracts are washed with an aqueous solution of lithium chloride (5%), dried over magnesium sulfate, filtered and concentrated under reduced pressure to afford the title compound (0.49 g, 0.7 mmol, 81% yield, 60% purity) as a brown oil. MS m/z 334.0 (M+Na).

Preparation 5

Synthesis of 5-methyl-3-[[(2S,4S)-2-methyl-4-piperidyl]oxymethyl]-1,2,4-oxadiazole hydrochloride

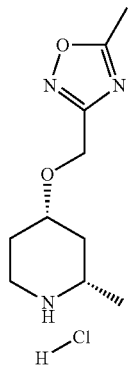

A flask containing tert-butyl (2S,4S)-2-methyl-4-[(5-methyl-1,2,4-oxadiazol-3-yl)methoxy]piperidine-1-carboxylate (4.03 g, 12.9 mmol) is submerged in an ice-water bath. To this flask is added a 4 M solution of hydrochloric acid in 1,4-dioxane (25.9 mL, 104 mmol) dropwise over 5 minutes with stirring, maintaining an internal temperature below 20° C. during the addition. The reaction mixture is stirred at room temperature for 1 hour, then is concentrated to give the title compound (3.56 g, 92% yield based on 83% purity measured by $^1$H NMR. MS m/z 212.0 (M+H).

Alternative Synthesis of 5-methyl-3-[[(2S,4S)-2-methyl-4-piperidyl]oxymethyl]-1,2,4-oxadiazole hydrochloride Add methanol (50 mL) to tert-butyl (2S,4S)-2-methyl-4-[(5-methyl-1,2,4-oxadiazol-3-yl)methoxy]piperidine-1-carboxylate (12.9 g, 0.041 mol). The mixture is cooled to 0° C. A 4M solution of hydrochloric acid in methanol (80 mL) is added dropwise to the cooled mixture, maintaining an internal temperature below 20° C. The reaction mixture is then stirred at room temperature for 18 hours. The mixture is then concentrated to remove solvent. Acetone (10 mL) is added and the mixture is stirred for 20 min. Tetrahydrofuran (40 mL) is added and the mixture is stirred for 3 hours. The solid is collected by filtration under nitrogen and the filtered solid cake is rinsed with tetrahydrofuran. The filtered solid is then dried under vacuum at 45° C. for 2 hours to give the title compound as a 90% purity. Recrystallization using acetone can increase purity of title compound to 95%.

Preparation 6

Synthesis of 5-methyl-3-[[(2S,4S)-2-methyl-4-piperidyl]oxymethyl]-1,2,4-oxadiazole

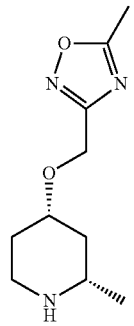

To a solution of tert-butyl (2S,4S)-2-methyl-4-[(5-methyl-1,2,4-oxadiazol-3-yl)methoxy]piperidine-1-carboxylate (0.49 g, 1.6 mmol) in dichloromethane (10 mL) under nitrogen is added trifluoroacetic acid (1.8 mL, 23 mmol). The mixture is stirred at room temperature for 3 h. The mixture is concentrated under reduced pressure to afford a yellow oil. The residue is dissolved in methanol (5 mL) and poured onto a cation exchange cartridge, eluted with methanol (2×10 mL) then a 2 M ammonia solution in methanol (10 mL). The filtrate is concentrated under reduced pressure to give title compound (0.3 g, 1.4 mmol, 91%). MS m/z 212.0 (M+H).

In other embodiments of the novel combinations and methods of the present invention, the OGA inhibitor a compound of Formula X:

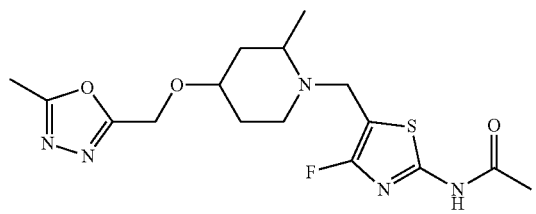

Formula X or a pharmaceutically acceptable salt thereof.

In addition, the present invention provides a compound of Formula Xa:

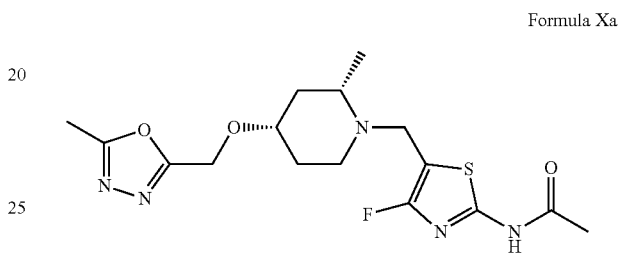

Formula Xa or a pharmaceutically acceptable salt thereof.

Certain configurations of Formula X, which comprise embodiments of the OGA inhibitor of the novel combinations and methods of the present invention, further include:

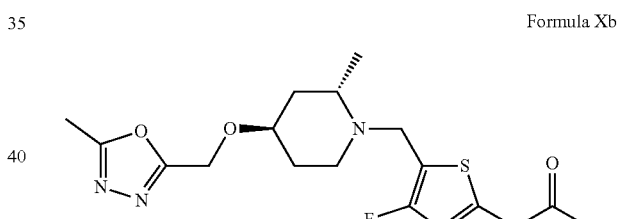

Formula Xb

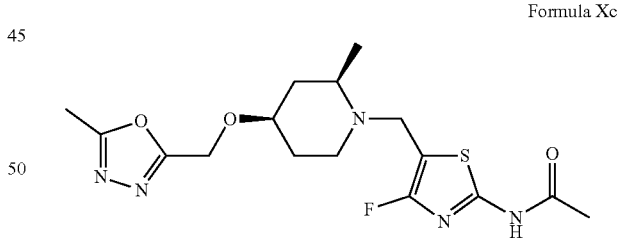

Formula Xc

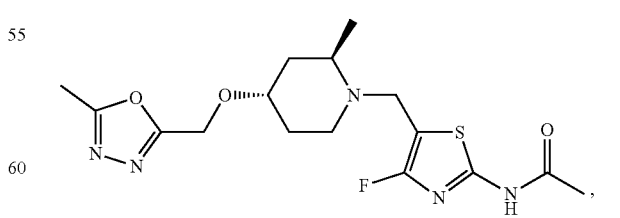

Formula Xd and pharmaceutically acceptable salts thereof.

The 5-methyl-1,3,4-oxadiazol-2-yl compound of Formula X wherein the methyl and oxygen substituents on the piperidine ring are in the cis or trans configuration, or pharmaceutically acceptable salt thereof, are included within the scope of the OGA inhibitor of the present novel combination. The present novel combination also contemplates all individual enantiomers and diasteromers, as well as mixtures of the enantiomers of 5-methyl-1,3,4-oxadiazol-2-yl compounds of the present invention, including racemates. Absolute configurations of 5-methyl-1,3,4-oxadiazol-2-yl compounds of the novel combinations and methods provided herein include:

N-[4-fluoro-5-[[(2S,4S)-2-methyl-4-[(5-methyl-1,3,4-oxadiazol-2-yl)methoxy]-1-piperidyl]methyl]thiazol-2-yl] acetamide, and pharmaceutically acceptable salts thereof, including with the free base, and including the crystalline form.

The 5-methyl-1,3,4-oxadiazol-2-yl compounds of the novel combinations and methods of the present invention, or salts thereof, may be prepared by a variety of procedures known to one of ordinary skill in the art, some of which are illustrated in the schemes, preparations, and examples below. One of ordinary skill in the art recognizes that the specific synthetic steps for each of the routes described may be combined in different ways, or in conjunction with steps from different schemes, to prepare compounds of the invention, or salts thereof. The products of each step below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art. Without limiting the scope of the invention, the following schemes, preparations, and examples are provided to further illustrate the invention. In addition, one of ordinary skill in the art appreciates that the compounds of Formulas Xa, Xb, Xc, and Xd may be prepared by using starting material with the corresponding stereochemical configuration which can be prepared by one of skill in the art. For example, the preparations below utilize starting materials with the configuration corresponding ultimately to Formula Xa.

Preparation 7

Synthesis of 2-[[(2S,4S)-1-tert-butoxycarbonyl-2-methyl-4-piperidyl]oxy]acetic acid

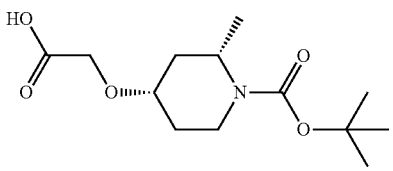 [SMILES: C[C@H]1C[C@@H](OCC(=O)O)CCN1C(=O)OC(C)(C)C]

2-Chloro-1-morpholino-ethanone (59.4 g, 363 mmol) is added to a solution of tert-butyl (2S,4S)-4-hydroxy-2-methyl-piperidine-1-carboxylate (52.1 g, 242 mmol) in acetonitrile (521 mL) at room temperature. The reaction mixture is stirred in an ice-water bath and sodium tert-butoxide (48.0 g, 484 mmol) is added in portions over 10 minutes, maintaining an internal temperature below 15° C. The reaction mixture is stirred at room temperature for 2 hours, then is added over 5 minutes to another flask containing saturated aqueous ammonium chloride solution (250 mL) and water (250 mL) with ice-water bath cooling, maintaining an internal temperature below 15° C. during the addition. The mixture is warmed to room temperature and extracted with methyl tert-butyl ether (2×500 mL), then the combined organics are washed with brine (300 mL). The combined organics are then dried over sodium sulfate, filtered, and concentrated to give a residue, which is combined with 2-propanol (414 mL) and 2M aqueous sodium hydroxide solution (303 mL, 605 mmol) at room temperature. The reaction mixture is stirred in a 47° C. heating block overnight with an internal temperature of 45° C. The reaction mixture is cooled to room temperature and concentrated to remove 2-propanol, then the mixture is diluted with water (50 mL). The mixture is extracted with methyl tert-butyl ether (250 mL), then the aqueous layer is cooled in an ice-water bath and acidified with acetic acid (55.6 mL, 968 mmol). The aqueous mixture is extracted with ethyl acetate (4×250 mL), then the combined organics are dried over sodium sulfate, filtered and concentrated to give a residue, which is concentrated from toluene (3×100 mL) to give the title compound (79.8 g). MS m/z 272.0 (M–H).

Preparation 8

Synthesis of tert-butyl (2S,4S)-4-[2-(2-acetylhydrazino)-2-oxo-ethoxy]-2-methyl-piperidine-1-carboxylate

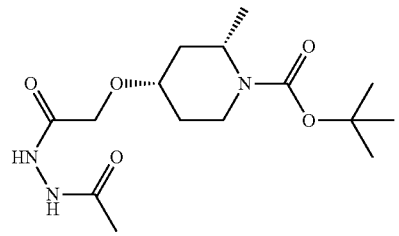 [SMILES: CC(=O)NNC(=O)CO[C@H]1CCN(C(=O)OC(C)(C)C)[C@@H](C)C1]

Tetrahydrofuran (798 mL) is added to a flask containing 2-[[(2S,4S)-1-tert-butoxycarbonyl-2-methyl-4-piperidyl] oxy]acetic acid (79.8 g, 224 mmol, 76.6 mass %) and the mixture is stirred in an ice-water bath with an internal temperature of 5° C. To the mixture is added 1,1'-carbonyldiimidazole (43.5 g, 268 mmol) in one portion and the reaction mixture is stirred at room temperature for 2 hours. An additional portion of 1,1'-carbonyldiimidazole (7.25 g, 44.7 mmol) is added and the reaction mixture is stirred at room temperature for 30 minutes. The reaction mixture is submerged in an ice-water bath and acetohydrazide (21.5 g, 291 mmol) is added in one portion, then the reaction mixture is stirred at room temperature overnight. The reaction mixture is stirred in an ice-water bath and saturated aqueous sodium bicarbonate solution (500 mL) is added over 2 minutes, maintaining an internal temperature below 15° C. The mixture is diluted with water (300 mL) and then is concentrated to remove tetrahydrofuran. The aqueous mixture is extracted with 2-methyltetrahydrofuran (4×500 mL). The combined organics are dried over sodium sulfate, filtered and concentrated to give a residue which is combined with ethyl acetate (200 mL) and heptane (200 mL). The mixture is stirred at room temperature for 30 minutes, then is diluted with heptane (200 mL) and the mixture is stirred vigorously at room temperature for an additional 30 minutes, then is filtered. The filtered solid is dried under vacuum at 40° C. for 2 hours to give the first crop of the title compound (71.5 g). The filtrate is refiltered and the filtered solid is dried under a stream of nitrogen gas at room temperature for 15 minutes to give the second crop of the title compound (1.98 g). The majority of the first crop of product (71.1 g, 216 mmol, unknown purity) and the second crop of product (1.97 g, 5.98 mmol, unknown purity) are combined with tert-butyl methyl ether (731 mL) and the mixture is stirred in a 45° C. heating block for 30 minutes at an internal temperature 40° C., then is cooled to room temperature over 1 hour with stirring and the mixture is filtered. The filtered solid is dried under vacuum at room temperature under a stream of nitrogen gas for 30 minutes to give the title compound (53.7 g). MS m/z 352.0 (M+Na).

Preparation 9

Synthesis of tert-butyl (2S,4S)-2-methyl-4-[(5-methyl-1,3,4-oxadiazol-2-yl)methoxy]piperidine-1-carboxylate

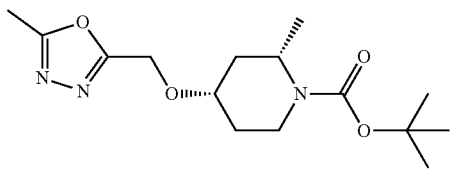 [SMILES: Cc1nnc(CO[C@H]2CCN(C(=O)OC(C)(C)C)[C@@H](C)C2)o1]

To a solution of tert-butyl (2S,4S)-4-hydroxy-2-methyl-piperidine-1-carboxylate (0.5 g, 2 mmol) in N,N-dimethylformamide (5 mL) under nitrogen at room temperature is added portionwise sodium tert-butoxide (0.92 g, 9.28 mmol). The resulting reaction mixture is stirred at room temperature for 40 min. The reaction mixture is cooled to 0° C. and 2-(chloromethyl)-5-methyl-1,3,4-oxadiazole (0.416 g, 3.14 mmol) is added. The resulting solution stirred at room temperature overnight. The reaction mixture is concentrated in vacuo and the residue diluted with water. The mixture is extracted with 3 portions of ethyl acetate. The combined organic extracts are dried over magnesium sulfate, filtered and concentrated under reduced pressure to afford a crude oil. The residue is taken up in dimethyl sulfoxide (to a total volume of 2 ml), and purified by prep-HPLC (Phenomenex Gemini-NX 10 Micron 30*100 mm C-18) (CH₃CN & Water with 10 mM ammonium bicarbonate adjusted to pH 9 with ammonium hydroxide, 15% to 100% CH₃CN over 7 min at 50 ml/min) (1 injection) (204 nm) to afford the title compound (0.028 g, 0.089 mmol, 4%). MS m/z 312.0 (M+H).

Alternative Synthesis of tert-butyl (2S,4S)-2-methyl-4-[(5-methyl-1,3,4-oxadiazol-2-yl)methoxy]piperidine-1-carboxylate

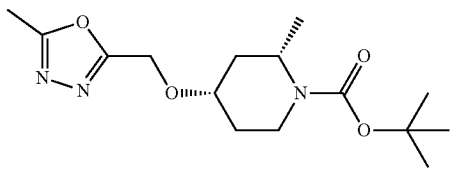 [SMILES: Cc1nnc(CO[C@H]2CCN(C(=O)OC(C)(C)C)[C@@H](C)C2)o1]

To a flask is added tert-butyl (2S,4S)-4-[2-(2-acetylhydrazino)-2-oxo-ethoxy]-2-methyl-piperidine-1-carboxylate (53.7 g, 163 mmol) and acetonitrile (537 mL) and the slurry is stirred at room temperature. To the mixture is added N,N-diisopropylethylamine (114 mL, 652 mmol) in one portion and p-toluenesulfonyl chloride (77.7 g, 408 mmol) in three portions over 5 minutes with water bath cooling. The reaction mixture is stirred at room temperature overnight, then is cooled in an ice-water bath and N',N'-dimethyl-ethane-1,2-diamine (21.8 g, 245 mmol) is added dropwise over 10 minutes, maintaining an internal temperature below 15° C. The reaction mixture is stirred at room temperature for 30 minutes, then is diluted with saturated aqueous citric acid solution (50 mL), ethyl acetate (500 mL) and water (450 mL) at room temperature. The layers are separated and the organic layer is washed with a mixture of saturated aqueous citric acid solution (50 mL) and water (450 mL). The organic layer is washed with saturated aqueous sodium bicarbonate solution (500 mL) and the aqueous layer is then extracted with ethyl acetate (500 mL). The combined organics are dried over sodium sulfate, filtered and concentrated to give a residue, which is passed through a short pad of silica gel (400 g), eluting with 25% ethyl acetate in heptane (2×500 mL fractions) and then with ethyl acetate (5×500 mL fractions). The product-containing fractions are concentrated to give the title compound (53.3 g). MS m/z 312.2 (M+H).

Preparation 10

Synthesis of 5-methyl-5-[[(2S,4S)-2-methyl-4-piperidyl]oxymethyl]-1,3,4-oxadiazole 2,2,2-trifluoroacetic acid

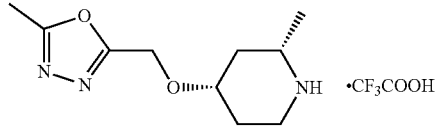

To a solution of tert-butyl (2S,4S)-2-methyl-4-[(5-methyl-1,3,4-oxadiazol-2-yl)methoxy]piperidine-1-carboxylate (0.0275 g, 0.0883 mmol) in dichloromethane (3 mL) under nitrogen is added trifluoroacetic acid (0.035 mL, 0.45 mmol). The mixture is stirred at room temperature overnight. The mixture is concentrated under reduced pressure afford the title compound (0.04 g, 84%). MS m/z 212.0 (M+H).

Preparation 11

Synthesis of 2-methyl-5-[[(2S,4S)-2-methyl-4-piperidyl]oxymethyl]-1,3,4-oxadiazole

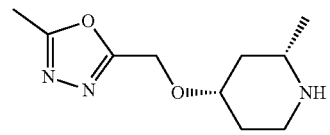

To a flask is added tert-butyl (2S,4S)-2-methyl-4-[(5-methyl-1,3,4-oxadiazol-2-yl)methoxy]piperidine-1-carboxylate (52.9 g, 170 mmol) and dichloromethane (265 mL) at room temperature. The reaction mixture is stirred in an ice-water bath at an internal temperature of 5° C. and trifluoroacetic acid (3500 mmol, 265 mL) is added dropwise over 5 minutes, maintaining an internal temperature below 10° C. The reaction mixture is stirred at room temperature for 15 minutes, then is concentrated to give a residue, which is diluted with water (300 mL) and methyl tert-butyl ether (300 mL). The layers are separated and the aqueous layer is stirred in an ice-water bath and basified with 50% aqueous sodium hydroxide solution (20 mL), maintaining an internal temperature below 10° C. during the addition. The mixture is extracted with dichloromethane (4×300 mL) and the combined organics are dried over sodium sulfate, filtered and concentrated to give the title compound (30.5 g). MS m/z 212.2 (M+H).

It should be appreciated that individual isomers, enantiomers, and diastereomers of the OGA inhibitor compounds, provided herein as part of the novel combinations and methods of the instant invention, may be separated or resolved by one of ordinary skill in the art at any convenient point in the synthesis of compounds of the invention, by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994).

A pharmaceutically acceptable salt of the OGA inhibitor compounds of the invention can be formed, for example, by reaction of an appropriate free base of a compound of the invention and an appropriate pharmaceutically acceptable acid in a suitable solvent under standard conditions well known in the art. The formation of such salts is well known and appreciated in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977).

EXAMPLES

The following examples are intended to illustrate but not to limit the invention.

Expression of Engineered Anti-Tau Antibodies

Engineered anti-Tau antibodies of the present invention can be expressed and purified essentially as follows. A glutamine synthetase (GS) expression vector containing the DNA sequence of SEQ ID NO.12 (encoding LC amino acid sequence of SEQ ID NO.1) and the DNA sequence of SEQ ID NO.11 (encoding HC amino acid sequence of SEQ ID NO.2) is used to transfect a Chinese hamster ovary cell line (CHO) by electroporation. The expression vector encodes an SV Early (Simian Virus 40E) promoter and the gene for GS. Expression of GS allows for the biochemical synthesis of glutamine, an amino acid required by the CHO cells. Post-transfection, cells undergo bulk selection with 50 μM L-methionine sulfoximine (MSX). The inhibition of GS by MSX is utilized to increase the stringency of selection. Cells with integration of the expression vector cDNA into transcriptionally active regions of the host cell genome can be selected against CHO wild type cells, which express an endogenous level of GS. Transfected pools are plated at low density to allow for close-to-clonal outgrowth of stable expressing cells. The masterwells are screened for antibody expression and then scaled up in serum-free, suspension cultures to be used for production.

Clarified medium, into which the antibody has been secreted, is applied to a Protein A affinity column that has been equilibrated with a compatible buffer, such as phosphate buffered saline (pH 7.4). The column is washed with 1M NaCl to remove nonspecific binding components. The bound anti-Tau antibodies are eluted, for example, with sodium citrate at pH (approx.) 3.5 and fractions are neutralized with 1M Tris buffer. Anti-Tau antibody fractions are detected, such as by SDS-PAGE or analytical size-exclusion, and then are pooled. Soluble aggregate and multimers may be effectively removed by common techniques, including size exclusion, hydrophobic interaction, ion exchange, or hydroxyapatite chromatography. The anti-Tau antibody of the present invention is concentrated and/or sterile filtered using common techniques. The purity of the anti-Tau antibody after these chromatography steps is greater than 95%. The anti-Tau antibody of the present invention may be immediately frozen at −70° C. or stored at 4° C. for several months.

Binding Kinetics and Affinity of Anti-Tau Antibody

Surface Plasmon Resonance (SPR) assay, measured with a BIACORE® 2000 instrument (primed with HBS-EP+ running buffer (GE Healthcare, 10 mM Hepes pH7.4+150 mM NaCl+3 mM EDTA+0.05% surfactant P20) at 25° C.), is used to measure binding of an exemplified anti-Tau antibody (having both HCs of SEQ ID NO.2 and both LCs of SEQ ID NO.1) to both human monomeric (e.g., native or non-aggregate) tau and human tau aggregates (both having the amino acid sequence as set forth in SEQ ID NO.13).

Except as noted, all reagents and materials are from BIACORE® AB (Upsala, Sweden). A CM5 chip containing immobilized protein A (generated using standard NHS-EDC amine coupling) on all four flow cells (FC) is used to employ a capture methodology. Antibody samples are prepared at 0.5 μg/mL by dilution into running buffer. Monomeric tau and fibril tau are prepared to concentrations of 2000, 1000, 500, 250, 125, 62.5, 31.25, 15.63, 7.82, 3.91, 1.95, and 0 (blank) nM by dilution into running buffer. Each analysis cycle consists of: (1) capturing antibody samples on separate flow cells (FC2, FC3, and FC4); (2) injection of 250 μL, (300 sec) of either monomeric tau or tau fibril aggregate over respective FC at a rate of 50 μL/min; (3) return to buffer flow for 20 mins. to monitor dissociation phase; (4) regeneration of chip surfaces with 25 μL (30 sec) injection of glycine, pH1.5; (5) equilibration of chip surfaces with a 50 μL (60 sec) injection of HBS-EP+.

Data of binding to tau aggregate is processed using standard double-referencing and fit to a 1:1 binding model using Biacore 2000 Evaluation software, version 4.1, to determine the association rate ($k_{on}$, $M^{-1}s^{-1}$ units), dissociation rate ($k_{off}$, $s^{-1}$ units), and $R_{max}$ (RU units). The equilibrium dissociation constant ($K_D$) was calculated from the relationship $K_D = k_{off}/k_{on}$, and is in molar units. Data of binding to monomeric tau cannot be determined accurately by SPR as described above due to rapid on- and off-rates. Therefore, $K_D$ for binding to monomeric tau is obtained by using a steady state binding fit model from plotting the concentration of antigen versus the response unit. Resulting binding data is provided in Table 1.

TABLE 1

SPR binding data to both human monomeric and aggregate tau.

| | | $k_{on}$ ($M^{-1}s^{-1}$ units) | $k_{off}$ ($M^{-1}s^{-1}$ units) | $K_D$* (nM) |
|---|---|---|---|---|
| Exemplified anti-Tau mAb | Monomeric Tau | Not detectable | Not detectable | 235 |
| | Tau Aggregate | 4.59e4 | <1e-5 | <0.22 |

*$K_D$ results are considered relative as the results are not normalized for influence of avidity.

The results provided in Table 1 demonstrate the exemplified anti-Tau antibody does possess significant binding affinity to tau aggregate and does not possess measureable binding to monomeric tau such that an affinity value can be accurately determined by Biacore analysis (due to rapid on- and off-rates).

Enzyme-Linked Immunosorbant Assay (ELISA) is used to determine relative binding affinity of the exemplified anti-Tau antibody (having both HCs of SEQ ID NO.2 and both LCs of SEQ ID NO.1) to aggregate tau fibrils from AD brain homogenates. AD brain homogenates are prepared from approx. 80 g of cortex from brain of AD patients. Briefly, buffer (TBS/1 mM PMSF/1× Complete® protease inhibitor cocktail (Roche, p/n. 11 697 498 001) and phosphatase inhibitor (ThermoFischer, p/n. 78428)) is added to the AD brain tissue at about 10 ml/1 g (tissue). Tissue is homogenized using a handheld Kinematica Polytron at speed 6-7. Tissue is then further homogenized using Parr Bomb (Parr Instrument, p/n. 4653) at 1500 psi of nitrogen for 30 mins. Homogenate is spun at 28,000 g (J14 Beckman rotor) for 30 min at 4° C. Supernatant is collected, pooled and run over a 4 cm high guard column of Sepharose 400 Superflow to remove larger debris, then run over 25 ml MC1-Affigel 10 column at a flow rate of 50-60 ml per hour, in order to purify MC1-binding tau fibrils. To maximize the recovery of purification, supernatants are recycled through MC-1 column over 18-20 hours at 4° C. Guard column is removed and MC1 column is washed with TBS with at least 40 column volumes. Bound tau aggregates are then eluted with 2 column volumes of 3M KSCN, collecting in approx. 1 ml fractions. Protein concentration in each eluted fraction is checked by microtiter plate Bradford assay. Fractions containing positive protein levels are pooled, concentrated to about 2 ml using Centricon (Millipore Ultracel-30K) at 4° C., and dialyzed using a Slide-A-Lyzer cassette (10K MWCO 3-12 ml, Pierce) overnight against 1 liter TBS. The concentration of tau within the tau fibrils purified from AD brain homogenate is measured by sandwich ELISA using DA-9 capture antibody and CP27 detection antibody.

Purified tau fibrils (50 µl) in PBS are coated on wells of 96-well plates (Coastar, p/n. 3690) at a concentration corresponding to 0.7 µg/ml of total tau. Plates are incubated overnight at 4° C., then washed three times with 150 µl of PBST (PBS containing 0.05% Tween-20), blocked in 100 µl BB3 (ImmunoChemistry Technology, p/n. 643) at room temperature for at least 1 hr (usually 2 hrs). Following blocking, the blocking buffer is removed from the wells. Exemplified anti-Tau antibody (having both HCs of SEQ ID NO.2 and both LCs of SEQ ID NO.1) is diluted in 0.25% casein buffer to 1000 nM stock, then diluted serially 23 times with two fold dilutions. 50 µl of stock and serially diluted antibody are added to separate wells and incubated for 2 hours at room temperature, after which the plate is washed four times with 200 µl PBST per well. 50 µl of anti-human IgG-HRP antibodies (diluted at 1:4000 into 0.25% casein buffer) is added and incubated for 1 hour at room temperature, after which the plate is washed with 200 µl PBST per well 4 times. 50 µl of TMB/H2O2 is added and incubated at room temperature for about 10 minutes. Reaction is stopped by adding 50 µl stop solution (2N H2SO4) and colorimetric signal is measured at 450 nm. Data is input into Prism 6 (GraphPad) program and $EC_{50}$ values are generated using a nonlinear regression curve fit and sigmoidal dose response. Results are presented in Table 2.

TABLE 2

| $EC_{50}$ Comparison of Binding to Purified AD Tau Fibrils | |
| --- | --- |
| Antibody Assayed | $EC_{50}$ (pM) |
| Exemplified anti-Tau mAb | 6.8 |

As reflected in Table 2, exemplified tau monoclonal antibody of the present invention demonstrates significant affinity (as measured by $EC_{50}$) to purified tau fibrils.

Ex Vivo Target Engagement Studies

Binding of exemplified anti-Tau antibody (having both HCs of SEQ ID NO.2 and both LCs of SEQ ID NO.1) to aggregated tau derived from human brains is determined through immunohistochemistry staining of formalin-fixed paraffin-embedded (FFPE) brain sections obtained from: a "normal" individual (displaying minimal tau aggregation); an AD patient (displaying severe tau aggregation and NFT formation pathology); a PD patient (displaying severe tau aggregation). Staining is also performed on brain sections derived from a "control" wild type mouse that possess no human tau in order to determine background non-specific staining levels.

FFPE sections are de-paraffinized and rehydrated. Thereafter, antigen retrieval (using the Lab Vision PT module system, Thermo Scientific) is performed on the sections which includes heating sections in citrate buffer (Thermo Scientific, p/n. TA-250-PM1X) for 20 minutes at 100° C. then cooling the sections in dH2O. Sections are then exposed to the following seven incubation steps (at room temp.): (1) 10 min. in 0.03% H2O2; (2) 30 min. in 1:20 dilution of normal goat serum (Vector Labs., p/n. S-1000) diluted in PBST; (3) 60 min. in exemplified anti-Tau antibody (normalized to 1 mg/ml, then diluted in PBST to a dilution of 1:4000 before incubation with sections); (4) 30 min. in rabbit anti-human IgG4 (raised against the Fc region of the exemplified antibody) at a concentration of 1.1 µg/ml in PBST; (5) 30 min. in 1:200 dilution of biotinylated goat anti-rabbit IgG (Vector Labs., p/n. BA-1000) diluted in PBST; (6) 30 min. in avidin-biotin complex solution (Vector Labs., p/n. PK-7100); (7) 5 min. in 3,3'-diaminobenzidine (Vector Labs., p/n. SK-4105). Sections are washed between each of the above 7 steps using PBST. Following the seven incubation steps above, sections are counterstained with haematoxylin, dehydrated and cover-slipped. For mouse "control" tissue sections the above protocol is modified in incubation step (3) by using a 1:8000 dilution (as opposed to a 1:4000 dilution) of exemplified anti-Tau antibody; and by replacing incubation steps (4) and (5) with a single 30 min. 1:200 dilution of biotinylated goat anti-human IgG (Vector Labs. p/n. BA-3000) in PBST.

Following procedures substantially as described above, an analysis of the binding of the exemplified anti-Tau antibody to tau derived from human brains is performed. Results are provided in Table 3.

TABLE 3

Semi-quantitative analysis of binding to aggregated tau in FFPE AD brain sections.

| | Severity of aggregated tau detected as measured by semi quantitative scoring scheme (severe, +++; moderate, ++; mild, +; negative, −) | | | |
|---|---|---|---|---|
| | WT control (murine) | Normal control (human) | Alzheimer's disease | Pick's disease |
| Exemplified anti-Tau mAb | − | + | +++ | +++ |

The results provided in Table 3 reflect that exemplified anti-Tau antibody demonstrates significantly higher levels of staining to aggregated tau, from both AD and PD patients, in hippocampal brain sections as compared to the control sample. Further, because AD and PD are characterized by distinct splicing variants of the gene encoding tau, these results support a conclusion that exemplified anti-Tau antibody specifically binds the conformational epitope comprising amino acid residues 7-9 and 312-322 of human tau (residue numbering based on the exemplified human tau of SEQ ID NO.13) common to tau aggregates of both AD and PD.

In Vivo Neutralization of Tau Aggregate Propagation

Homogenate brain stem preps from approx. 5 month old P301S mice are known to, upon injection into hippocampus of normal 10 week old female P301S mice, induce aggregation of native, non-aggregate tau, demonstrating a propagation-like effect of tau aggregation. Homogenate preps of brain stem tissue from 4.5 to 5 month old P301S mice are prepared substantially the same as described above.

Normal 10 week old female P301S mice are injected in the left hemisphere of the hippocampus with 5 µl homogenate brain prep and either: 7.5 µg exemplified anti-Tau antibody (having both HCs of SEQ ID NO.2 and both LCs of SEQ ID NO.1) (N=12); or 7.5 µg of control human IgG4 antibody (N=11). Four weeks post-injection, the mice are sacrificed and the left and right hemispheres are collected, paraffin embedded, and 6 µm serial sections are mounted on glass slides. Slides containing bregma (A−P=−2.30) are de-paraffinized, embedded tissue is rehydrated, and antigen retrieval is performed by heating slide to 100° C. for 20 min. in citrate buffer. Slides are cooled in dH$_2$O and incubated at room temperature according to the following steps: (a) 10 min. in (0.03%) H2O2; (b) 30 min. in a 1:20 dilution of normal goat serum; (c) 60 min. in a 1:8000 dilution of PG-5 antibody (diluted in PBST)(PG-5 antibody obtained from the lab of Dr. Peter Davies, Albert Einstein College of Medicine of Yeshiva University; PG-5 antibody specifically binds serine at residue 409 of tau when phosphorylated, residue numbering based on the exemplified human tau of SEQ ID NO.13); (d) 30 min. in a 1:200 dilution of biotinylated goat anti-mouse IgG antibody (diluted in PBST); (e) 30 min. in avidin-biotin complex solution; and (f) 5 min. in 3,3'-diaminobenzidine. PBST is used for washing between the respective steps. Following the 5 min. incubation in 3,3'-diaminobenzidine, sections are counterstained with haematoxylin, then rehydrated and cover-slipped. Staining signal is measured by Scanscope AT Slide Scanner (Aperio) at 20× magnification. PG-5 immunoreactivity is quantified and expressed as a percentage using the positive pixel algorithm of Imagescope Software (v. 11.1.2.780, Aperio). Results are provided in Table 4.

TABLE 4

Mean % PG-5 immunoreactivity in left and right hippocampus, respectively.

| | (% PG-5 Immunoreactivity) | |
|---|---|---|
| | Left Hippocampus | Right Hippocampus |
| Exemplified anti-Tau mAb | 2.52 ± 0.49 SEM | 0.63 ± 0.13 SEM |
| Control IgG4 Ab | 6.38 ± 0.93 SEM | 1.88 ± 0.31 SEM |

The results provided in Table 4 demonstrate the exemplified anti-Tau antibody reduces the level of tau aggregation in both the left and right hippocampus as compared to the control IgG4 antibody. As shown, the exemplified anti-Tau antibody produces a 60.5% greater reduction in tau aggregation in the left hippocampus, and a 66.5% greater reduction in tau aggregation in the right hippocampus, respectively, compared to control IgG4 antibody. These results demonstrate the exemplified anti-Tau antibody possesses neutralizing activity against propagation of tau aggregation.

5-methyl-1,2,4-oxadiazol-3-yl OGA Inhibitors

Example 1

Synthesis of N-[4-fluoro-5-[[(2S,4S)-2-methyl-4-[(5-methyl-1,2,4-oxadiazol-3-yl)methoxy]-1-piperidyl]methyl]thiazol-2-yl]acetamide

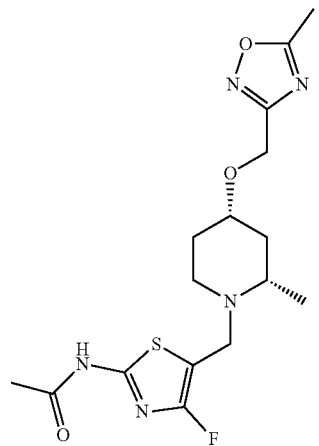 [SMILES: CC(=O)Nc1nc(F)c(CN2CC[C@H](OCc3noc(C)n3)C[C@@H]2C)s1]

N-(4-Fluoro-5-formyl-thiazol-2-yl)acetamide (28.3 g, 150 mmol) is added to 5-methyl-3-[[(2S,4S)-2-methyl-4-piperidyl]oxymethyl]-1,2,4-oxadiazole hydrochloride (48.7 g, 185 mmol, 94% purity) in ethyl acetate (707 mL) at room temperature. The reaction mixture is stirred at room temperature and N,N-diisopropylethylamine (34.1 mL, 195 mmol) is added dropwise over 1 minute, then sodium triacetoxyborohydride (98.5 g, 451 mmol) is added in one portion. The reaction mixture is stirred in a 31° C. heating block overnight with an internal temperature of 30° C., then is cooled in an ice-water bath to an internal temperature of 5° C. To the mixture is added 2 M aqueous hydrochloric acid solution (226 mL) over 15 minutes, maintaining an internal temperature below 10° C. To the mixture is added water (250 mL) and the mixture is stirred at room temperature for 5 minutes. The layers are separated and the organic layer is extracted with a mixture of 2 M aqueous hydrochloric acid solution (28 mL) in water (50 mL). The first aqueous layer is stirred in an ice-water bath and 50% aqueous sodium hydroxide solution (25.7 mL) is added dropwise over 10 minutes, maintaining an internal temperature below 10° C. The mixture is diluted with saturated aqueous sodium bicarbonate solution (100 mL), then is stirred at room temperature for 10 minutes and then is extracted with ethyl acetate (3×400 mL). The combined organics are dried over sodium sulfate, filtered and concentrated to give a residue. The second aqueous layer from the extraction with aqueous hydrochloric acid is diluted with 2-methyltetrahydrofuran (200 mL) and the mixture is passed through a short pad of diatomaceous earth. The filtrate is transferred to a separating funnel and the layers are separated. The aqueous layer is stirred in an ice-water bath and 50% aqueous sodium hydroxide solution (3.15 mL) is added dropwise over 5 minutes, maintaining an internal temperature below 10° C. The mixture is diluted with saturated aqueous sodium bicarbonate solution (10 mL), then is stirred at room temperature for 5 minutes and then is extracted with ethyl acetate (3×40 mL) and 10% isopropanol in ethyl acetate (100 mL). The combined organics are dried over sodium sulfate, filtered and concentrated to give a residue, which is combined with the residue from the first part of the workup. The combined residue is passed through a pad of silica gel (350 g) eluting with ethyl acetate (3.5 L) and the filtrate is concentrated to give a residue (45.8 g).

The residue (47.5 g of combined lots, 123.9 mmol) is purified by flash chromatography, eluting with 50-100% ethyl acetate in heptane. The product-containing fractions are concentrated to residue, which is suspended in a 1:1 mixture of methyl-tert-butyl ether and heptane (448 mL). The mixture is stirred in a 46° C. heating block for 30 minutes at an internal temperature of 45° C., then is cooled to room temperature over 2 hours with stirring. The mixture is filtered, washing the solid with a 1:1 mixture of methyl-tert-butyl ether and heptane (30 mL). The filtered solid is dried under vacuum at 40° C. overnight to give the title compound (28.5 g). MS m/z 384.0 (M+H); $[\alpha]_D^{20}=+33.4°$ (C=0.26, methanol).

Alternative Synthesis of N-[4-fluoro-5-[[(2S,4S)-2-methyl-4-[(5-methyl-1,2,4-oxadiazol-3-yl)methoxy]-1-piperidyl]methyl]thiazol-2-yl]acetamide To a solution of N-(4-fluoro-5-formyl-thiazol-2-yl)acetamide (0.05 g, 0.28 mmol) and 5-methyl-3-[[(2S,4S)-2-methyl-4-piperidyl]oxymethyl]-1,2,4-oxadiazole (0.04 g, 0.19 mmol) in dichloromethane (10 mL) under nitrogen are added N,N-diisopropylethylamine (0.1 mL, 0.57 mmol) and sodium triacetoxyborohydride (0.12 g, 0.57 mmol). The reaction mixture is stirred at room temperature for 12 h. The reaction mixture is poured into a saturated aqueous solution of sodium bicarbonate (10 mL). The layers are separated and the aqueous phase is extracted with dichloromethane (2×10 mL). The combined organic extracts are dried over magnesium sulfate, filtered and concentrated under reduced pressure to afford an orange oil.

The residue is taken up in methanol (to a total volume of 9.8 ml), filtered and purified by prep-HPLC (Phenomenex Gemini-NX 10 Micron 50*150 mm C-18) ($CH_3CN$ & Water with 10 mM ammonium bicarbonate adjusted to pH 9 with ammonium hydroxide, 15% to 100% $CH_3CN$ over 10 min at 110 ml/min) (1 injection) (271/204 nm) to give the title compound (0.02 g, 0.05 mmol, 28%). MS m/z 384.2 (M+H).

Example 1A

Crystalline N-[4-fluoro-5-[[(2S,4S)-2-methyl-4-[(5-methyl-1,2,4-oxadiazol-3-yl)methoxy]-1-piperidyl] methyl]thiazol-2-yl]acetamide Suspend crude N-[4-fluoro-5-[[(2S,4S)-2-methyl-4-[(5-methyl-1,2,4-oxadiazol-3-yl)methoxy]-1-piperidyl]methyl] thiazol-2-yl]acetamide (29.9 g) in 448 mL of 50% methyl tert butyl ether in heptane at 46° C. for 30 minutes. Stir the mixture and cool to 19° C. over two hours before filtering following with a wash of 30 mL of 50% methyl tert butyl ether in heptane to provide the title compound (28.5 g, 95% yield).

X-Ray Powder Diffraction (XRPD) of Example 1A

The XRPD patterns of crystalline solids are obtained on a Bruker D4 Endeavor X-ray powder diffractometer, equipped with a CuKa source ($\lambda$=1.54060 Å) and a Vantec detector, operating at 35 kV and 50 mA. The sample is scanned between 4 and 40° in 2θ, with a step size of 0.0087° in 2θ and a scan rate of 0.5 seconds/step, and with 0.6 mm divergence, 5.28 mm fixed anti-scatter, and 9.5 mm detector slits. The dry powder is packed on a quartz sample holder and a smooth surface is obtained using a glass slide. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. (see, e.g. The U. S. Pharmacopeia 38—National Formulary 35 Chapter 941 Characterization of crystalline and partially crystalline solids by X-ray powder diffraction (XRPD) Official May 1, 2015). Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction patterns, collected at ambient temperature and relative humidity, are adjusted based on NIST 675 standard peaks at 8.85 and 26.77 degrees 2-theta.

A prepared sample of crystalline N-[4-fluoro-5-[[(2S,4S)-2-methyl-4-[(5-methyl-1,2,4-oxadiazol-3-yl)methoxy]-1-piperidyl]methyl]thiazol-2-yl]acetamide is characterized by an XRPD pattern using CuKa radiation as having diffraction peaks (2-theta values) as described in Table 1 below. Specifically the pattern contains a peak at 12.1° in combination with one or more peaks selected from the group consisting of 15.3°, 21.6°, 22.2°, 22.7°, 23.5°, 24.3°, and 26.8° with a tolerance for the diffraction angles of 0.2 degrees.

TABLE 5

X-ray powder diffraction peaks of crystalline N-[4-fluoro-
5-[[(2S,4S)-2-methyl-4-[(5-methyl-1,2,4-oxadiazol-3-yl)methoxy]-1-
piperidyl]methyl]thiazol-2-yl]acetamide, Example 1A.

| Peak | Angle (2-Theta °) +/− 0.2° | Relative Intensity (% of most intense peak) |
| --- | --- | --- |
| 1 | 7.7 | 9 |
| 2 | 10.1 | 9 |
| 3 | 12.1 | 100 |
| 4 | 15.3 | 50 |
| 5 | 18.3 | 11 |
| 6 | 19.3 | 13 |
| 7 | 21.6 | 16 |
| 8 | 22.2 | 16 |
| 9 | 22.7 | 16 |
| 10 | 23.5 | 30 |
| 11 | 24.3 | 35 |
| 12 | 26.8 | 27 |

5-methyl-1,3,4-oxadiazol-2-yl compounds OGA Inhibitors

Example 2

Synthesis of N-[4-fluoro-5-[[(2S,4S)-2-methyl-4-[(5-methyl-1,3,4-oxadiazol-2-yl)methoxy]-1-piperidyl]methyl]thiazol-2-yl]acetamide

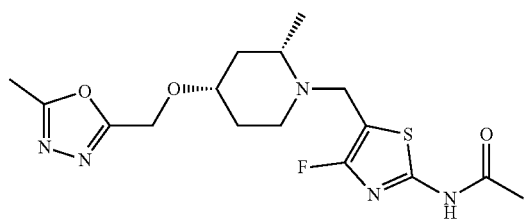 [SMILES: CC(=O)Nc1nc(F)c(CN2CC[C@H](OCc3nnc(C)o3)C[C@@H]2C)s1]

To a solution of 2-methyl-5-[[(2S,4S)-2-methyl-4-piperidyl]oxymethyl]-1,3,4-oxadiazole 2,2,2-trifluoroacetic acid (0.16 g, 0.7 mmol) in ethyl acetate (1 mL) under nitrogen is added N,N-diisopropylethylamine (0.021 mL, 0.12 mmol) and the solution stirred for 5 minutes. N-(4-fluoro-5-formyl-thiazol-2-yl)acetamide (0.04 g, 0.122 mmol) is added and stirred for 5 minutes, sodium triacetoxyborohydride (0.055 g, 0.25 mmol) is added and reaction mixture is warmed to 40° C. and stirred overnight. The mixture is concentrated under reduced pressure to afford a brown solid.

The residue is taken up in dimethyl sulfoxide (to a total volume of 1 ml) and purified by prep-HPLC (Phenomenex Gemini-NX 10 Micron 30*100 mm C-18) (CH₃CN & Water with 10 mM ammonium bicarbonate adjusted to pH 9 with ammonium hydroxide, 15% to 100% CH₃CN over 12 min at 100 ml/min) (1 injection) (271/204 nm) to give title compound (0.007 g, 14%). MS m/z 384.2 (M+H).

Alternative Synthesis of crystalline N-[4-fluoro-5-[[(2S,4S)-2-methyl-4-[(5-methyl-1,3,4-oxadiazol-2-yl)methoxy]-1-piperidyl]methyl]thiazol-2-yl]acetamide

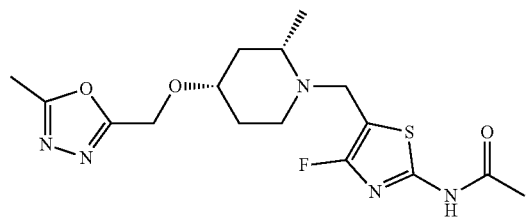 [SMILES: CC(=O)Nc1nc(F)c(CN2CC[C@H](OCc3nnc(C)o3)C[C@@H]2C)s1]

Sodium triacetoxyborohydride (59.1 g, 279 mmol) is added to a mixture of 2-methyl-5-[[(2S,4S)-2-methyl-4-piperidyl]oxymethyl]-1,3,4-oxadiazole (23.3 g, 93.0 mmol), ethyl acetate (438 mL) and N,N-diisopropylethylamine (32.4 mL, 186 mmol) at room temperature. The reaction mixture is stirred in a 31° C. heating block for 15 minutes with an internal temperature of 30° C., then N-(4-fluoro-5-formyl-thiazol-2-yl)acetamide (17.5 g, 93.0 mmol) is added portionwise over 5 minutes. The reaction mixture is stirred in a 31° C. heating block overnight with an internal temperature of 30° C., then is cooled in an ice-water bath to an internal temperature of 5° C. To the mixture is added 2M aqueous hydrochloric acid solution (140 mL) over 15 minutes, maintaining an internal temperature below 10° C. The mixture is stirred at room temperature for 15 minutes, then is diluted with water (50 mL) and ethyl acetate (20 mL) and the layers are separated. The organic layer is extracted with a mixture of 2M aqueous hydrochloric acid solution (35 mL) in water (100 mL). The combined aqueous layers are stirred in an ice-water bath and 50% aqueous sodium hydroxide solution (19.5 mL) is added dropwise over 10 minutes, maintaining an internal temperature below 10° C. The mixture is diluted with saturated aqueous sodium bicarbonate solution (50 mL), then is extracted with 2-methyltetrahydrofuran (3×200 mL). The combined organics are dried over sodium sulfate, filtered and concentrated to give a residue, which is purified by flash chromatography, eluting with 0-15% 2-propanol in dichloromethane. The product-containing fractions are concentrated to give a residue, which is concentrated from heptane (100 mL). The concentrated material is combined with 40% ethyl acetate in heptane (457 mL) and the mixture is stirred in a 50° C. heating block for 1 hour, then is cooled to room temperature and filtered. The filtered solid is dried under vacuum at 40° C. for 1 hour to give a first crop of product (22.9 g). The filtrate is concentrated to give a residue, which is combined with 40% ethyl acetate in heptane (50 mL) and the mixture is stirred in a 50° C. heating block for 30 minutes, then is cooled to room temperature and filtered. The filtered solid is combined with 50% ethyl acetate in heptane (33 mL) and the mixture is stirred in a 50° C. heating block for 1 hour, then is cooled to room temperature and filtered. The filtered solid is dried under vacuum at 40° C. for 1 hour to give a second crop of product (2.50 g).

A combination of lots including the first and second crops of product (29.3 g, 76.4 mmol) is combined with ethyl acetate (117 mL) and heptane (117 mL) at room temperature. The mixture is stirred in a 51° C. heating block for 30 minutes at an internal temperature of 50° C., then is cooled to room temperature and filtered. The filtered solid is dried overnight at 40° C. under vacuum to give the title compound (26.7 g) as a crystalline solid. MS m/z 384.0 (M+H), $[\alpha]_D^{20}$=+39° (C=0.2, methanol).

X-Ray Powder Diffraction (XRPD) of crystalline N-[4-fluoro-5-[[(2S,4S)-2-methyl-4-[(5-methyl-1,3,4-oxadiazol-2-yl)methoxy]-1-piperidyl]methyl]thiazol-2-yl]acetamide Crystalline N-[4-fluoro-5-[[(2S,4S)-2-methyl-4-[(5-methyl-1,3,4-oxadiazol-2-yl)methoxy]-1-piperidyl]methyl]thiazol-2-yl]acetamide (218 mg) is dissolved in 1.25 mL of methanol at 60° C. for 5 minutes. The solution is cooled to ambient temperature with stirring for 20 minutes. The resulting solid is isolated by vacuum filtration. The final solid product is 163 mg or 75% yield.

The XRD patterns of crystalline solids are obtained on a Bruker D4 Endeavor X-ray powder diffractometer, equipped with a CuKa source ($\lambda$=1.54060 Å) and a Vantec detector, operating at 35 kV and 50 mA. The sample is scanned between 4 and 40° in 2θ, with a step size of 0.0087° in 2θ and a scan rate of 0.5 seconds/step, and with 0.6 mm divergence, 5.28 mm fixed anti-scatter, and 9.5 mm detector slits. The dry powder is packed on a quartz sample holder and a smooth surface is obtained using a glass slide. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The U. S. Pharmacopeia 38—National Formulary 35 Chapter <941> Characterization of crystalline and partially crystalline solids by X-ray powder diffraction (XRPD) Official May 1, 2015. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction patterns, collected at ambient temperature and relative humidity, were adjusted based on NIST 675 standard peaks at 8.85 and 26.77 degrees 2-theta.

Thus, crystalline N-[4-fluoro-5-[[(2S,4S)-2-methyl-4-[(5-methyl-1,3,4-oxadiazol-2-yl)methoxy]-1-piperidyl]methyl]thiazol-2-yl]acetamide is characterized by an XRD pattern using CuKa radiation as having diffraction peaks (2-theta values) as described in Table 1. More specifically, the pattern preferably contains a peak at 13.5° in combination with one or more peaks selected from the group consisting of 5.8°, 13.0°, 14.3°, 17.5°, 20.4°, 21.4°, and 22.2° with a tolerance for the diffraction angles of 0.2 degrees.

TABLE 6

X-ray powder diffraction peaks of crystalline N-[4-fluoro-5-[[(2S,4S)-2-methyl-4-[(5-methyl-1,3,4-oxadiazol-2-yl)methoxy]-1-piperidyl]methyl]thiazol-2-yl]acetamide.

| Peak | Angle (2-Theta °) | Intensity (%) |
| --- | --- | --- |
| 1 | 5.8 | 78 |
| 2 | 9.2 | 18 |
| 3 | 11.7 | 24 |
| 4 | 13.0 | 34 |
| 5 | 13.5 | 100 |
| 6 | 14.3 | 39 |
| 7 | 17.5 | 50 |
| 8 | 18.3 | 30 |
| 9 | 19.7 | 11 |
| 10 | 20.1 | 14 |
| 11 | 20.4 | 43 |
| 12 | 20.7 | 17 |
| 13 | 21.4 | 37 |
| 14 | 22.0 | 17 |
| 15 | 22.2 | 39 |
| 16 | 23.1 | 12 |
| 17 | 23.8 | 16 |
| 18 | 23.9 | 25 |
| 19 | 24.9 | 19 |
| 20 | 25.2 | 30 |
| 21 | 28.7 | 10 |
| 22 | 37.0 | 11 |

In Vitro Human OGA Enzyme Assay
Generation of OGA Proteins

The nucleotide sequence encoding full-length human O-GlcNAc-β-N-acetylglucosaminidase (NM_012215) is inserted into pFastBacl (Invitrogen) vector with an N-terminal poly-histidine (HIS) tag. Baculovirus generation is carried out according to the Bac-to-Bac Baculovirus Expression system (Invitrogen) protocol. Sf9 cells are infected at 1.5×10$^6$ cells/mL using 10 mL of P1 virus per Liter of culture and incubated at 28° C. for 48 hrs. Cells are spun down, rinsed with PBS and the pellets stored at −80° C. The above OGA protein (His-OGA) is purified as follows: 4 L of cells are lysed in 200 mL of buffer containing 50 mM Tris, pH 8.0, 300 mM NaCl, 10% glycerol, 10 mM Imidazol, 1 mM Dithiothreitol (DTT), 0.1% Triton™ X-100, 4 tablets of protease inhibitors (complete EDTA-Free, Roche) for 45 min at 4° C. This cell lysate is then spun for 40 min at 16500 rpm at 4° C., and supernatant incubated with 6 mL of Ni-NTA resin (nickel-nitrilotriacetic acid) for 2 hours at 4° C.

Resin is then packed onto column and washed with 50 mM Tris, pH 8.0, 300 mM NaCl, 10% glycerol, 10 mM Imidazole, 0.1% Triton™ X-100, 1 mM DTT, followed by 50 mM Tris, pH 8.0, 150 mM NaCl, 10 mM Imidazol, 10% glycerol, 1 mM DTT. The proteins are eluted with 50 mM Tris, pH 8.0, 150 mM NaCl, 300 mM Imidazole, 10% glycerol, 1 mM DTT. Pooled His-OGA containing fractions are concentrated to 6 ml and loaded onto Superdex75 (16/60). The protein is eluted with 50 mM Tris, pH 8.0, 150 mM NaCl, 10% glycerol, 2 mM DTT. Fractions containing His-OGA are pooled and protein concentration measured with BCA (Bradford Colorimetric Assay).

OGA Enzyme Assay

The OGA enzyme catalyses the removal of O-GlcNAc from nucleocytoplasmic proteins. To measure this activity Fluorescein di-N-acetyl-β-N-acetyl-D-glucosaminide (FD-GlcNAc, Kim, Eun Ju; Kang, Dae Ook; Love, Dona C.; Hanover, John A. Carbohydrate Research (2006), 341(8), 971-982) is used as a substrate at a final concentration of 10 µM (in the 96 well assay format) or 6.7 µM (in the 384 well assay format). This fluorogenic substrate becomes fluorescent upon cleavage by OGA, so that the enzyme activity can be measured by the increase in fluorescence detected at 535 nm (excitation at 485 nm).

The assay buffer is prepared to give a final concentration of 50 mM $H_2NaPO_3$—$HNa_2PO_3$, 0.01% bovine serum albumin and 0.01% Triton™ X-100 in water, at pH 7. The final enzyme concentration is 3 nM (in the 96 well assay format) or 3.24 nM (in the 384 well assay format). Both assay formats yield essentially equivalent results.

Compounds to be tested are diluted in pure dimethyl sulfoxide (DMSO) using ten point concentration response curves. Maximal compound concentration in the reaction mixture is 30 µM. Compounds at the appropriate concentration are pre-incubated with OGA enzyme for 30 minutes before the reaction is started by the addition of substrate. Reactions are allowed to proceed for 60 minutes at room temperature. Then, without stopping the reaction, fluorescence is read. $IC_{50}$ values are calculated by plotting the normalized data vs. log of the compound and fitting the data using a four parameter logistic equation.

The compound of Example 1 was tested essentially as described above and exhibited an $IC_{50}$ of 2.36 nM±0.786 (n=8). This data demonstrates that the compound of Example 1 inhibits OGA enzyme activity in vitro.

The compound of Example 2 was also tested essentially as described above and exhibited an $IC_{50}$ of 2.13 nM±0.89 (n=5). This result demonstrates that the compound of Example 2 inhibits OGA enzyme activity in vitro.

Whole Cell Assay for Measuring the Inhibition of OGA Enzyme Activity
Cell Plating:

Utilizing standard conditions known in the art, TRex-293 cells modified for inducible expression of the P301S-1N4R form of the microtubule associated protein tau are generated and maintained in growth media, consisting of DMEM High Glucose (Sigma #D5796), supplemented with 10% Tetracyclin-free Fetal Bovine Serum (FBS, Sigma F2442), 20 mM HEPES, 5 µg/mL Blasticidin (Life Technologies #A11139-03) and 200 µg/mL Zeocin (Life Technologies #R250-01). For the experiments, cells are plated in growth media at 10,000-14,000 cells per well in a Corning Biocoat (356663) 384 well plate coated with poly-D-Lysine, and incubated 20-24 h in a cell incubator at 37° C./5% $CO_2$. Experiments are performed without inducing Tau expression.

Compound Treatment:

Compounds to be tested are serially diluted 1/3 in pure DMSO using ten point concentration response curves and further diluted in growth media. 20-24 h after plating, cells are treated with test compound in growth media; maximal compound concentration is 15 µM (0.15% DMSO). The maximum inhibition is defined by replicate measurements of 15 uM Thiamet G and the minimum inhibition is defined by replicate measurements of 0.15% DMSO treatment. The cells are returned to the incubator at 37° C./5% $CO_2$ for 20-24 hours. Compounds are tested in duplicates within each plate.

Immunostaining:

After 20-24 hours of compound treatment, the media is removed from the assay plate and 25 µL of 3.7% Formaldehyde solution (Sigma #F1635) in DPBS (Sigma #D8537; Dulbecco's phosphate buffered saline) is added to each well and incubated for 30 minutes. The cells are then washed once with DPBS and then permeabilized with 0.1% Triton™ X-100 (Sigma #T9284). After 30 minutes, cells are washed twice with DPBS and then blocking solution (1% BSA/DPBS/0.1% Triton™ X-100) is added to each well and incubated for 60 minutes. The blocking solution is removed and a 0.40-0.33 µg/mL solution of O-GlcNAc Protein antibody (RL2 clone, Thermo, MA1072) in blocking solution is added to the cells and allowed to sit overnight at 2-8° C. The next day, the cells are washed twice with DPBS and the secondary antibody, Alexa Fluor 488 goat anti-mouse IgG (Life Technologies #A11001) at 2 ug/mL in DPBS is added to each well and allowed to sit at room temperature for 90 min. The secondary antibody is removed, cells washed twice with DPBS and a solution of DAPI (Sigma #D9564; 4',6-diamidino-2-phenyindole, dilactate) and RNase (Sigma, R6513) in DPBS at a concentration of 1 and 50 ug/mL, respectively, is added to each well. The plate is sealed, incubated for one hour and analyzed on an Acumen eX3 hci (TTP Labtech). All the incubations and washing steps described above are done at room temperature, except for the primary antibody.

Analysis and Results:

The plates are analyzed on an Acumen eX3 instrument using a 488 and 405 nm excitation lasers and two emission filters FL2 (500-530 nm) and FL1 (420-490 nm). The FL2 filter is the signal corresponding to the O-GlcNAc Protein antibody (RL2 clone) and the FL1 filter is the signal corresponding to the cell nuclei (DAPI). The ratio Total FL2/Total FL1 (Total fluorescence of each well without object or population selection) is used for data analysis. The data are normalized to a maximum inhibition as referenced by a 15 µM treatment of Thiamet G and a minimum inhibition as achieved by a 0.15% DMSO treatment. The data are fitted with a non-linear curve fitting application (4-parameters logistic equation) and $IC_{50}$ values are calculated and reported.

The compound of Example 1 was tested essentially as described above and exhibited an $IC_{50}$ of 21.9 nM±7.3 (n=5). This data demonstrates that the compound of Example 1 inhibits OGA enzyme activity in a cellular assay.

The compound of Example 2 was also tested essentially as described above and exhibited an $IC_{50}$ of 22.6 nM±7.3 (n=3). This result demonstrates that the compound of Example 2 inhibits OGA enzyme activity in a cellular assay.

In Vivo Murine Combination Study

The following Example demonstrates how a study could be designed to verify (in animal models) that the combination of the anti-Tau antibodies of the present invention, in combination with the OGA inhibitors of the present invention, may be useful for treating a disease characterized by aberrant tau aggregation, such as AD, PSP and CBS. It should be understood however, that the following descriptions are set forth by way of illustration and not limitation, and that various modifications may be made by one of ordinary skill in the art.

In order to evaluate the impact of tau hyperphosphorylation and aggregation reduction by exemplified OGA inhibitors, and the tau aggregation propagation neutralization of exemplified anti-Tau antibody, in a combination therapy as described herein, tau transgenic mice (e.g., JNPL3 or Tg4510) are used (alternatively, progeny from a Tau/APP transgenic mouse line, derived from the cross of a tau transgenic line with an APP transgenic mouse line (e.g., Tg2576 or PDAPP or APP knock-in) may be used). As known in the field, Tau antibodies of the present invention induce an immunogenic response in Tg4510 mice and thus a surrogate murine tau antibody, preferably targeting the same conformational epitope and reflecting similar levels of improved affinity relative to the exemplified tau monoclonal antibody of Example 1, should be used. Mice may be divided into treatment groups consisting of: (a) control antibody (e.g., 15 mg/kg) or vehicle; (b) OGA inhibitor and control; (c) anti-Tau antibody (e.g., 15 mg/kg) and control; and (d) OGA inhibitor and anti-Tau antibody (e.g., 15 mg/kg). Antibody may be administered intraperitoneal, for example, twice weekly.

Following the treatment period, mice may be sacrificed and brain and spinal cord tissue collected. Tau aggregate pathology may be assessed as described above or with volumetric Mill. This study may show that the combination therapy of an OGA inhibitor and an anti-Tau antibody results in reduction of tau pathology (for example in hippocampus of mice), hyperphosphorylation and aggregation and reduction in tau aggregate propagation and preferably with synergistic interaction.

In Vivo Combination Study

The following Example demonstrates how a study could be designed to verify that the combination of OGA inhibitor of the present invention, in combination with an anti-Tau antibody of the present invention, may be useful for treating a disease characterized by aberrant tau aggregation, such as AD, PSP and CBS. It should be understood however, that the following descriptions are set forth by way of illustration and not limitation, and that various modifications may be made by one of ordinary skill in the art.

In order to evaluate the impact of tau hyperphosphorylation and aggregation reduction by exemplified OGA inhibitors, and the tau aggregation propagation neutralization of exemplified anti-Tau antibody, in a combination therapy as described herein, delay in disease progression may be assessed by biomarkers and/or cognitive and functional decline assessment using validated rating scales.

Patients may be divided into treatment groups consisting of double-blinded placebo and combination therapy groups. Combination therapy groups are administered an effective amount of an OGA inhibitor, in combination with an effective amount of an anti-Tau antibody. Monotherapy groupings (monotherapy group of OGA inhibitor at the same dosage as the OGA inhibitor in the combination group; and monotherapy group of anti-Tau antibody at the same dosage as the anti-Tau antibody in the combination therapy group) may be included to further elucidate the contributions of each individual molecule to the disease modification. Moreover, treatment groups may be characterized based on a diagnosis of pre-clinical or clinical AD, or based on a diagnosis that the patient (although asymptomatic for AD) possesses an AD disease-causing genetic mutation. For example, groups may include one or more of: (a) asymptomatic but AD-causing genetic-mutation positive; (b) prodromal AD; (c) mild AD; (d) moderate AD; and (e) severe AD. Each treatment group may receive the respective treatment (e.g., once per month for the anti-Tau antibody and daily for the OGA inhibitor) for a treatment period of 9 months to 18 months.

Following the treatment period, AD neurodegeneration may be assessed through one or more of the following biomarker assessments: (a) Tau PET imagining (assessment of NFT accumulation); (b) volumetric MRI (assessment of neuroanatomical atrophy); (c) FDG-PEG PET imagining (assessment of hypometabolism); (d) florbetapir perfusion PET imagining (assessment of hypometabolism); (e) CSF tau concentration (assessment of neurodegeneration); and/or (f) CSF phosphorylated-Tau concentration (assessment of neurodegeneration). Additionally, one or more validated rating scales assessing the cognitive and functional decline of each treatment group may be applied, for example ADAS-cog, MMSE, CDR-SB, ADCS-ADL, and Functional Activities Questionnaire (FAQ).

In some embodiments, for clinical trials in patients diagnosed with PSP or CBS, patients may receive treatments for a period of 6 months to 18 months. Neurodegeneration may be assessed through one or more of the following biomarker assessments: (a) DAT or AV-133 imaging (dopaminergic system degeneration); (b) volumetric MRI (assessment of neuroanatomical atrophy); (c) FDG-PEG PET imagining (assessment of hypometabolism); and/or (d) CSF neurofilament light chain, neurogranin, tau, p-tau (assessment of neurodegeneration). Additionally, one or more validated rating scales assessing the cognitive and functional decline of each treatment group may be applied, for example PSP-RS, MMSE, SEADL, CGI-C, MoCA.

This study may show that the combination therapy of an OGA inhibitor of the present invention and an anti-Tau antibody of the present invention may result in reduction of tau hyperphosphorylation and aggregation and reduction in tau aggregate propagation.

```
Sequences
LC of exemplified anti-Tau antibody
                                       SEQ ID NO: 1
EIVLTQSPGTLSLSPGERATLSCRSSQSLVHSNQNTYLHWYQQKPGQA

PRLLIYKVDNRFSGIPDRFSGSGSGTDFTLTISRLEPEDFAVYYCSQS

TLVPLTFGGGTKVEIKRTVAAPSVFIFPPSDEQLKSGTASVVCLLNNF

YPREAKVQWKVDNALQSGNSQESVTEQDSKDSTYSLSSTLTLSKADYE

KHKVYACEVTHQGLSSPVTKSFNRGEC

HC of exemplified anti-Tau antibody
                                       SEQ ID NO: 2
EVQLVQSGAEVKKPGESLKISCKGSGYTFSNYWIEWVRQMPGKGLEWM

GEILPGSDSIKYEKNFKGQVTISADKSISTAYLQWSSLKASDTAMYYC

ARRGNYVDDWGQGTLVTVSSASTKGPSVFPLAPCSRSTSESTAALGCL

VKDYFPEPVTVSWNSGALTSGVHTFPAVLQSSGLYSLSSVVTVPSSSL

GTKTYTCNVDHKPSNTKVDKRVESKYGPPCPPCPAPEAAGGPSVFLFP

PKPKDTLMISRTPEVTCVVVDVSQEDPEVQFNWYVDGVEVHNAKTKPR

EEQFNSTYRVVSVLTVLHQDWLNGKEYKCKVSNKGLPSSIEKTISKAK

GQPREPQVYTLPPSQEEMTKNQVSLTCLVKGFYPSDIAVEWESNGQPE

NNYKTTPPVLDSDGSFFLYSRLTVDKSRWQEGNVFSCSVMHEALHNHY

TQKSLSLSLG

LCDR1 of exemplified anti-Tau antibody
                                       SEQ ID NO: 3
RSSQSLVHSNQNTYLH LCDR2 of exemplified anti-Tau antibody
                                       SEQ ID NO: 4
YKVDNRFS LCDR3 of exemplified anti-Tau antibody
                                       SEQ ID NO: 5
SQSTLVPLT HCDR1 of exemplified anti-Tau antibody
                                       SEQ ID NO: 6
KGSGYTFSNWIE HCDR2 of exemplified anti-Tau antibody
                                       SEQ ID NO: 7
EILPGSDSIKYEKNFKG HCDR3 of exemplified anti-Tau antibody
                                       SEQ ID NO: 8
```

ARRGNYVDD

LCVR of exemplified anti-Tau antibody
SEQ ID NO: 9
EIVLTQSPGTLSLSPGERATLSCRSSQSLVHSNQNTYLHWYQQKPGQA
PRLLIYKVDNRFSGIPDRFSGSGSGTDFTLTISRLEPEDFAVYYCSQS
TLVPLTFGGGTKVEIK HCVR of exemplified anti-Tau antibody
SEQ ID NO: 10
EVQLVQSGAEVKKPGESLKISCKGSGYTFSNYWIEWVRQMPGKGLEWM
GEILPGSDSIKYEKNFKGQVTISADKSISTAYLQWSSLKASDTAMYYC
ARRGNYVDDWGQGTLVTVSS Nucleotide Sequence Encoding the Exemplified
HC (SEQ ID NO: 2)
SEQ ID NO: 11
gaggtgcagctggtgcagtctggagcagaggtgaaaaagcccggggag tctctgaagatctcctgtaaggttctggctacacattcagtaactac tggatagagtgggtgcgccagatgcccgggaaaggcctggagtggatg ggggagattttacctggaagtgatagtattaagtacgaaaagaatttc aagggccaggtcaccatctcagccgacaagtccatcagcaccgcctac ctgcagtggagcagcctgaaggcctcggacaccgccatgtattactgt gcgagaaggggggaactacgtggacgactggggccagggcaccctggtc accgtctcctcagcttctaccaagggcccatcggtcttcccgctagcg ccctgctccaggagcacctccgagagcacagccgccctgggctgcctg gtcaaggactacttccccgaaccggtgacggtgtcgtggaactcaggc gccctgaccagcggcgtgcacaccttcccggctgtcctacagtcctca ggactctactccctcagcagcgtggtgaccgtgccctccagcagcttg ggcacgaagacctacacctgcaacgtagatcacaagcccagcaacacc aaggtggacaagagagttgagtccaaatatggtcccccatgcccaccc tgcccagcacctgaggccgccggggggaccatcagtcttcctgttcccc ccaaaacccaaggacactctcatgatctcccggacccctgaggtcacg tgcgtggtggtggacgtgagccaggaagaccccgaggtccagttcaac tggtacgtggatggcgtggaggtgcataatgccaagacaaagccgcgg gaggagcagttcaacagcacgtaccgtgtggtcagcgtcctcaccgtc ctgcaccaggactggctgaacggcaaggagtacaagtgcaaggtctcc aacaaaggcctcccgtcctccatcgagaaaaccatctccaaagccaaa gggcagccccgagagccacaggtgtacaccctgcccccatcccaggag gagatgaccaagaaccaggtcagcctgacctgcctggtcaaaggcttc taccccagcgacatcgccgtggagtgggaaagcaatgggcagccggag aacaactacaagaccacgcctcccgtgctggactccgacggctccttc ttcctctacagcaggctaaccgtggacaagagcaggtggcaggagggg aatgtcttctcatgctccgtgatgcatgaggctctgcacaaccactac acacagaagagcctctccctgtctctgggt Nucleotide Sequence Encoding the Exemplified
LC (SEQ ID NO: 1)
SEQ ID NO: 12
gaaattgtgttgacgcagtctccaggcacccctgtctttgtctccaggg gaaagagccaccctctcctgcagatctagtcagagccttgtacacagt aatcagaacacctatttacattggtaccagcagaaacctggccaggct cccaggctcctcatctataaagttgacaaccgattttctggcatccca gacaggttcagtggcagtgggtctgggacagacttcactctcaccatc agcagactggagcctgaagattttgcagtgtattactgttctcaaagt acactggttccgctcacgttcggcggagggaccaaggtggagatcaaa cggaccgtggctgcaccatctgtcttcatcttcccgccatctgatgag cagttgaaatctggaactgcctctgttgtgtgcctgctgaataacttc tatcccagagaggccaaagtacagtggaaggtggataacgcccctccaa tcgggtaactcccaggagagtgtcacagagcaggacagcaaggacagc acctacagcctcagcagcaccctgacgctgagcaaagcagactacgag aaacacaaagtctacgcctgcgaagtcacccatcagggcctgagctcg cccgtcacaaagagcttcaacaggggagagtgc Amino Acid Sequence of Human, Full-Length Tau
SEQ ID NO: 13
MAEPRQEFEVMEDHAGTYGLGDRKDQGGYTMHQDQEGDTDAGLKESPL
QTPTEDGSEEPGSETSDAKSTPTAEDVTAPLVDEGAPGKQAAAQPHTE
IPEGTTAEEAAGIGDTPSLEDEAAGHVTQARMVSKSKDGTGSDDKKAKG
ADGKTKIATPRGAAPPGQKGQANATRIPAKTPPAPKTPPSSGEPPKSG
DRSGYSSPGSPGTPGSRSRTPSLPTPPTREPKKVAVVRTPPKSPSSAK
SRLQTAPVPMPDLKNVKSKIGSTENLKHQPGGGKVQIINKKLDLSNVQ
SKCGSKDNIKHVPGGGSVQIVYKPVDLSKVTSKCGSLGNIHHKPGGGQ
VEVKSEKLDFKDRVQSKIGSLDNITHVPGGGNKKIETHKLTFRENAKA
KTDHGAEIVYKSPVVSGDTSPRHLSNVSSTGSIDMVDSPQLATLADEV
SASLAKQGL

We claim:

1. A method of treating a patient having a disease characterized by aberrant tau aggregation, comprising administering to a patient in need of such treatment an effective amount of an anti-Tau antibody in combination with an effective amount of an O-GlcNAcase ("OGA") inhibitor, wherein the OGA inhibitor is a compound of formula:

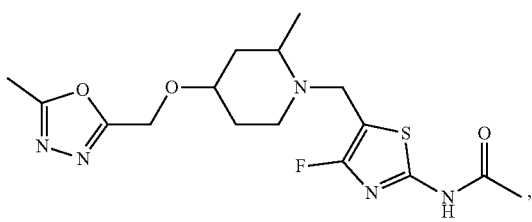 [SMILES: CC(=O)Nc1nc(F)c(CN2CCC(OCc3nnc(C)o3)CC2C)s1]

or a pharmaceutically acceptable salt thereof.

2. The method of claim 1, wherein the disease characterized by formation of aberrant tau aggregation is selected from a group consisting of clinical or pre-clinical Alzheimer's disease ("AD"), progressive supranuclear palsy ("PSP") and corticobasal syndrome ("CBS").

3. The method of claim 1, wherein the methyl at position 2 of the OGA inhibitor is in the cis configuration relative to the oxygen at position 4 on the piperidine ring:

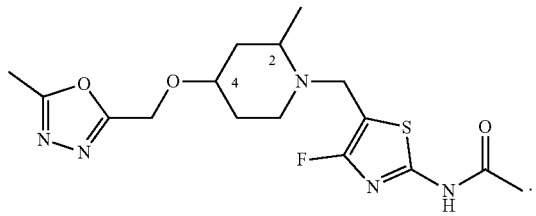 [SMILES: CC(=O)Nc1nc(F)c(CN2CCC(OCc3nnc(C)o3)CC2C)s1]

4. The method of claim 3, wherein the OGA inhibitor is N-[4-fluoro-5-[[(2S,4S)-2-methyl-4-[(5-methyl-1,2,4-oxadiazol-3-yl)methoxy]-1-piperidyl]methyl]thiazol-2-yl]acetamide.

5. The method of claim 4, wherein the OGA inhibitor is crystalline.

6. The method of claim 5, wherein the compound is characterized by a peak in the X-ray powder diffraction spectrum, at diffraction angle 2-theta of 12.1° in combination with one or more peaks selected from the group consisting of 15.3°, 21.6°, 22.2°, 22.7°, 23.5°, 24.3°, and 26.8°, with a tolerance for the diffraction angles of 0.2 degrees.

* * * * *

UNITED STATES PATENT AND TRADEMARK OFFICE
CERTIFICATE OF CORRECTION

PATENT NO. : 11,839,654 B2
APPLICATION NO. : 17/141667
DATED : December 12, 2023
INVENTOR(S) : Hayashi et al.

Page 1 of 2

It is certified that error appears in the above-identified patent and that said Letters Patent is hereby corrected as shown below:

On the Title Page

Column 1 item (54) (Title), delete "COMBINATION THERAPY" and insert -- COMBINATION THERAPY COMPRISING AN ANTI-TAU ANTIBODY AND AN O-GLCNACASE INHIBITOR FOR THE TREATMENT OF TAUOPATHIES --.

In the Specification

Column 1, delete "COMBINATION THERAPY" and insert -- COMBINATION THERAPY COMPRISING AN ANTI-TAU ANTIBODY AND AN O-GLCNACASE INHIBITOR FOR THE TREATMENT OF TAUOPATHIES --.

In the Claims

Claim 1, Column 49, Lines 8-18:

Delete " 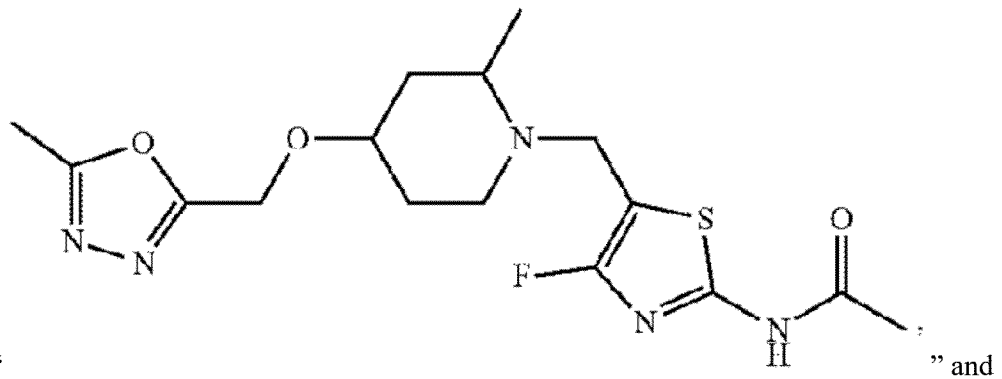 " and

Signed and Sealed this
Tenth Day of September, 2024

Katherine Kelly Vidal
*Director of the United States Patent and Trademark Office*

CERTIFICATE OF CORRECTION (continued)
U.S. Pat. No. 11,839,654 B2

Insert --

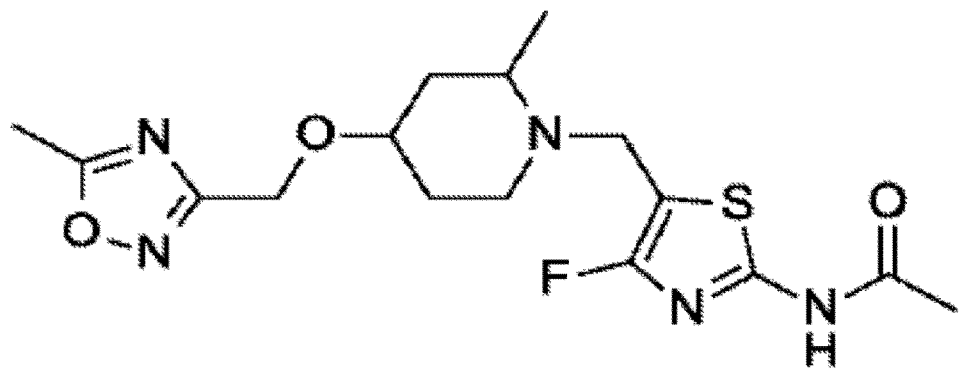

--.

Claim 3, Column 50, Lines 1-10:

Delete "

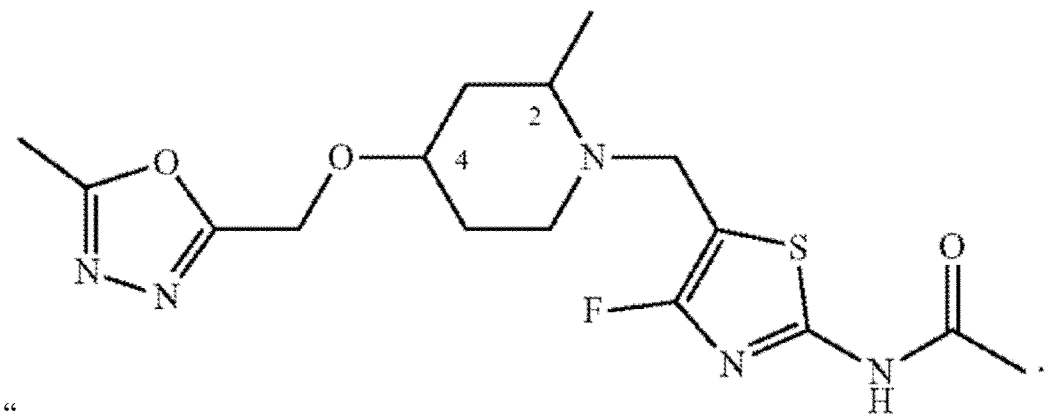

" and

Insert --

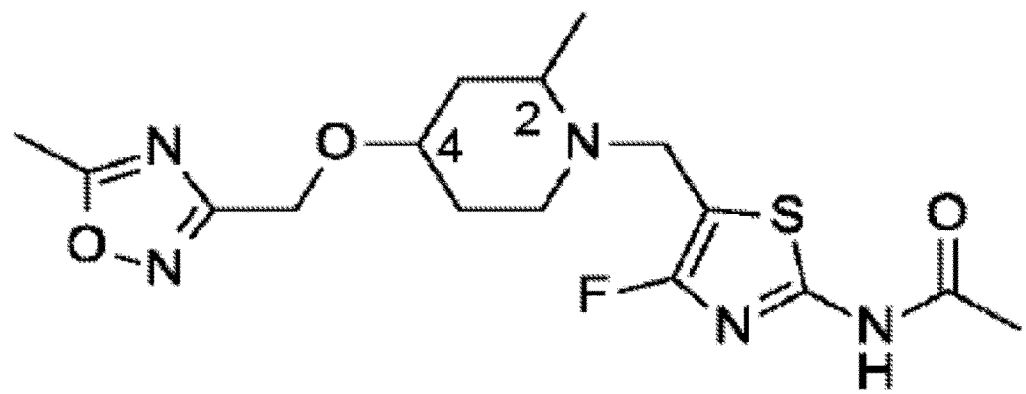

--.

SEQUENCE LISTING

<160> NUMBER OF SEQ ID NOS: 13

<210> SEQ ID NO 1
<211> LENGTH: 219
<212> TYPE: PRT
<213> ORGANISM: Artificial Sequence
<220> FEATURE:
<223> OTHER INFORMATION: LC of exemplified anti-Tau antibody

<400> SEQUENCE: 1

Glu Ile Val Leu Thr Gln Ser Pro Gly Thr Leu Ser Leu Ser Pro Gly
1               5                   10                  15

Glu Arg Ala Thr Leu Ser Cys Arg Ser Ser Gln Ser Leu Val His Ser
            20                  25                  30

Asn Gln Asn Thr Tyr Leu His Trp Tyr Gln Gln Lys Pro Gly Gln Ala
        35                  40                  45

Pro Arg Leu Leu Ile Tyr Lys Val Asp Asn Arg Phe Ser Gly Ile Pro
    50                  55                  60

Asp Arg Phe Ser Gly Ser Gly Ser Gly Thr Asp Phe Thr Leu Thr Ile
65                  70                  75                  80

Ser Arg Leu Glu Pro Glu Asp Phe Ala Val Tyr Tyr Cys Ser Gln Ser
                85                  90                  95

Thr Leu Val Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 2
<211> LENGTH: 442
<212> TYPE: PRT
<213> ORGANISM: Artificial Sequence
<220> FEATURE:
<223> OTHER INFORMATION: HC of exemplified anti-Tau antibody

<400> SEQUENCE: 2

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Ser Asn Tyr
            20                  25                  30

Trp Ile Glu Trp Val Arg Gln Met Pro Gly Lys Gly Leu Glu Trp Met
        35                  40                  45

Gly Glu Ile Leu Pro Gly Ser Asp Ser Ile Lys Tyr Glu Lys Asn Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Gly Asn Tyr Val Asp Asp Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu

```
                130             135             140
Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Lys Thr Tyr Thr Cys Asn Val Asp His Lys Pro Ser Asn Thr
                195                 200                 205

Lys Val Asp Lys Arg Val Glu Ser Lys Tyr Gly Pro Pro Cys Pro Pro
210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
                260                 265                 270

Trp Tyr Val Asp Gly Val Glu Val His Asn Ala Lys Thr Lys Pro Arg
                275                 280                 285

Glu Glu Gln Phe Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
                340                 345                 350

Glu Met Thr Lys Asn Gln Val Ser Leu Thr Cys Leu Val Lys Gly Phe
                355                 360                 365

Tyr Pro Ser Asp Ile Ala Val Glu Trp Glu Ser Asn Gly Gln Pro Glu
                370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
                420                 425                 430

Thr Gln Lys Ser Leu Ser Leu Ser Leu Gly
                435                 440

<210> SEQ ID NO 3
<211> LENGTH: 16
<212> TYPE: PRT
<213> ORGANISM: Artificial Sequence
<220> FEATURE:
<223> OTHER INFORMATION: LCDR1 of exemplified anti-Tau antibody

<400> SEQUENCE: 3

Arg Ser Ser Gln Ser Leu Val His Ser Asn Gln Asn Thr Tyr Leu His
1               5                   10                  15

<210> SEQ ID NO 4
<211> LENGTH: 8
<212> TYPE: PRT
<213> ORGANISM: Artificial Sequence
<220> FEATURE:
<223> OTHER INFORMATION: LCDR2 of exemplified anti-Tau antibody
```

```
<400> SEQUENCE: 4

Tyr Lys Val Asp Asn Arg Phe Ser
1               5

<210> SEQ ID NO 5
<211> LENGTH: 9
<212> TYPE: PRT
<213> ORGANISM: Artificial Sequence
<220> FEATURE:
<223> OTHER INFORMATION: LCDR3 of exemplified anti-Tau antibody

<400> SEQUENCE: 5

Ser Gln Ser Thr Leu Val Pro Leu Thr
1               5

<210> SEQ ID NO 6
<211> LENGTH: 13
<212> TYPE: PRT
<213> ORGANISM: Artificial Sequence
<220> FEATURE:
<223> OTHER INFORMATION: HCDR1 of exemplified anti-Tau antibody

<400> SEQUENCE: 6

Lys Gly Ser Gly Tyr Thr Phe Ser Asn Tyr Trp Ile Glu
1               5                   10

<210> SEQ ID NO 7
<211> LENGTH: 17
<212> TYPE: PRT
<213> ORGANISM: Artificial Sequence
<220> FEATURE:
<223> OTHER INFORMATION: HCDR2 of exemplified anti-Tau antibody

<400> SEQUENCE: 7

Glu Ile Leu Pro Gly Ser Asp Ser Ile Lys Tyr Glu Lys Asn Phe Lys
1               5                   10                  15

Gly

<210> SEQ ID NO 8
<211> LENGTH: 9
<212> TYPE: PRT
<213> ORGANISM: Artificial Sequence
<220> FEATURE:
<223> OTHER INFORMATION: HCDR3 of exemplified anti-Tau antibody

<400> SEQUENCE: 8

Ala Arg Arg Gly Asn Tyr Val Asp Asp
1               5

<210> SEQ ID NO 9
<211> LENGTH: 112
<212> TYPE: PRT
<213> ORGANISM: Artificial Sequence
<220> FEATURE:
<223> OTHER INFORMATION: LCVR of exemplified anti-Tau antibody

<400> SEQUENCE: 9

Glu Ile Val Leu Thr Gln Ser Pro Gly Thr Leu Ser Leu Ser Pro Gly
1               5                   10                  15

Glu Arg Ala Thr Leu Ser Cys Arg Ser Ser Gln Ser Leu Val His Ser
                20                  25                  30

Asn Gln Asn Thr Tyr Leu His Trp Tyr Gln Gln Lys Pro Gly Gln Ala
            35                  40                  45
```

```
Pro Arg Leu Leu Ile Tyr Lys Val Asp Asn Arg Phe Ser Gly Ile Pro
    50                  55                  60

Asp Arg Phe Ser Gly Ser Gly Ser Gly Thr Asp Phe Thr Leu Thr Ile
65                  70                  75                  80

Ser Arg Leu Glu Pro Glu Asp Phe Ala Val Tyr Tyr Cys Ser Gln Ser
                85                  90                  95

Thr Leu Val Pro Leu Thr Phe Gly Gly Gly Thr Lys Val Glu Ile Lys
            100                 105                 110

<210> SEQ ID NO 10
<211> LENGTH: 116
<212> TYPE: PRT
<213> ORGANISM: Artificial Sequence
<220> FEATURE:
<223> OTHER INFORMATION: HCVR of exemplified anti-Tau antibody

<400> SEQUENCE: 10

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Ser Asn Tyr
            20                  25                  30

Trp Ile Glu Trp Val Arg Gln Met Pro Gly Lys Gly Leu Glu Trp Met
        35                  40                  45

Gly Glu Ile Leu Pro Gly Ser Asp Ser Ile Lys Tyr Glu Lys Asn Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Gly Asn Tyr Val Asp Asp Trp Gly Gln Gly Thr Leu Val
            100                 105                 110

Thr Val Ser Ser
        115

<210> SEQ ID NO 11
<211> LENGTH: 1326
<212> TYPE: DNA
<213> ORGANISM: Artificial Sequence
<220> FEATURE:
<223> OTHER INFORMATION: Nucleotide Sequence Encoding the Exemplified HC
      (SEQ ID NO: 2)

<400> SEQUENCE: 11
gaggtgcagc tggtgcagtc tggagcagag gtgaaaaagc ccggggagtc tctgaagatc      60
tcctgtaagg gttctggcta cacattcagt aactactgga tagagtgggt gcgccagatg     120
cccgggaaag gcctggagtg gatggggag attttacctg gaagtgatag tattaagtac      180
gaaaagaatt tcaagggcca ggtcaccatc tcagccgaca agtccatcag caccgcctac     240
ctgcagtgga gcagcctgaa ggcctcggac accgccatgt attactgtgc gagaaggggg     300
aactacgtgg acgactgggg ccagggcacc ctggtcaccg tctcctcagc ttctaccaag     360
ggcccatcgg tcttccccgct agcgccctgc tccaggagca cctccgagag cacagccgcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cgaagaccta cacctgcaac     600
gtagatcaca agcccagcaa caccaaggtg gacaagagag ttgagtccaa atatggtccc     660
```

```
ccatgcccac cctgcccagc acctgaggcc gccggggggac catcagtctt cctgttcccc    720
ccaaaaccca aggacactct catgatctcc cggacccctg aggtcacgtg cgtggtggtg    780
gacgtgagcc aggaagaccc cgaggtccag ttcaactggt acgtggatgg cgtggaggtg    840
cataatgcca agacaaagcc gcgggaggag cagttcaaca gcacgtaccg tgtggtcagc    900
gtcctcaccg tcctgcacca ggactggctg aacggcaagg agtacaagtg caaggtctcc    960
aacaaaggcc tcccgtcctc catcgagaaa accatctcca agccaaagg gcagccccga   1020 gagccacagg tgtacaccct gcccccatcc caggaggaga tgaccaagaa ccaggtcagc   1080
ctgacctgcc tggtcaaagg cttctacccc agcgacatcg ccgtggagtg ggaaagcaat   1140
gggcagccgg agaacaacta caagaccacg cctcccgtgc tggactccga cggctccttc   1200
ttcctctaca gcaggctaac cgtggacaag agcaggtggc aggagggaa tgtcttctca   1260 tgctccgtga tgcatgaggc tctgcacaac cactacacac agaagagcct ctccctgtct   1320
ctgggt                                                             1326
```

<210> SEQ ID NO 12
<211> LENGTH: 657
<212> TYPE: DNA
<213> ORGANISM: Artificial Sequence
<220> FEATURE:
<223> OTHER INFORMATION: Nucleotide Sequence Encoding the Exemplified LC
      (SEQ ID NO: 1)

<400> SEQUENCE: 12

```
gaaattgtgt tgacgcagtc tccaggcacc ctgtctttgt ctccagggga aagagccacc     60
ctctcctgca gatctagtca gagccttgta cacagtaatc agaacaccta tttacattgg    120
taccagcaga aacctggcca ggctcccagg ctcctcatct ataaagttga caaccgattt    180
tctggcatcc cagacaggtt cagtggcagt gggtctggga cagacttcac tctcaccatc    240
agcagactgg agcctgaaga ttttgcagtg tattactgtt ctcaaagtac actggttccg    300
ctcacgttcg gcggagggac caaggtggag atcaaacgga ccgtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgc        657
```

<210> SEQ ID NO 13
<211> LENGTH: 441
<212> TYPE: PRT
<213> ORGANISM: Artificial Sequence
<220> FEATURE:
<223> OTHER INFORMATION: Amino Acid Sequence of Human, Full-Length Tau

<400> SEQUENCE: 13

```
Met Ala Glu Pro Arg Gln Glu Phe Glu Val Met Glu Asp His Ala Gly
 1               5                  10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60
```

```
Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
             85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
            130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
            165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
            195                 200                 205

Arg Ser Arg Thr Pro Ser Leu Pro Thr Pro Pro Thr Arg Glu Pro Lys
            210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
            245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
            275                 280                 285

Ser Lys Cys Gly Ser Lys Asp Asn Ile Lys His Val Pro Gly Gly Gly
            290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
            325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
            355                 360                 365

Lys Lys Ile Glu Thr His Lys Leu Thr Phe Arg Glu Asn Ala Lys Ala
            370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
            405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
            435                 440
```